(12) United States Patent
Coast

(10) Patent No.: US 11,682,095 B2
(45) Date of Patent: Jun. 20, 2023

(54) METHODS AND APPARATUS FOR PERFORMING AGRICULTURAL TRANSACTIONS

(71) Applicant: Mark Coast, San Diego, CA (US)

(72) Inventor: Mark Coast, San Diego, CA (US)

(*) Notice: Subject to any disclaimer, the term of this patent is extended or adjusted under 35 U.S.C. 154(b) by 367 days.

(21) Appl. No.: 16/986,182

(22) Filed: Aug. 5, 2020

(65) Prior Publication Data

US 2021/0264550 A1 Aug. 26, 2021

Related U.S. Application Data

(60) Provisional application No. 62/981,271, filed on Feb. 25, 2020.

(51) Int. Cl.
*G06Q 50/28* (2012.01)
*G06Q 30/018* (2023.01)
(Continued)

(52) U.S. Cl.
CPC .......... *G06Q 50/28* (2013.01); *G01G 17/00* (2013.01); *G01N 33/025* (2013.01);
(Continued)

(58) Field of Classification Search
CPC .... G06Q 50/28; G06Q 10/10; G06Q 30/0185; G06Q 50/02; G06Q 50/265; G01G 17/00;
(Continued)

(56) References Cited

U.S. PATENT DOCUMENTS 5,418,778 A 5/1995 Cummiskey et al.
9,436,923 B1 9/2016 Sriram et al.
(Continued)

FOREIGN PATENT DOCUMENTS

CA 3062485 A1 * 9/2019 .......... A23D 7/0053
CN 110619530 A * 12/2019
(Continued)

OTHER PUBLICATIONS

US 10,678,782 B2, 06/2020, Qiu (withdrawn)
(Continued)

*Primary Examiner* — Ashford S Hayles
(74) *Attorney, Agent, or Firm* — Wang Hardoon, P.C.

(57) ABSTRACT

Systems, apparatus, and methods for transacting, recording, validating and/or verifying agricultural products. The 2018 Farm Act rescinded industrial hemp from Schedule I of the Controlled Substances Act (CSA). Although industrial hemp has a variety of uses, the Government's biggest concern is the ingestion of tetrahydrocannabinol (THC) and cannabidiol (CBD). Commercial regulation typically balances a variety of factors: e.g., consumer protection, regulatory overhead, market competition, tax revenue, public policy, etc. In contrast, law enforcement has a singular purpose, and may go to extraordinary lengths to stop criminal activity. Various embodiments described herein provide a blockchain ledger-based supply chain that allows many commercial and regulatory entities to independently cooperate. Every transaction is permanently and transparently recorded within a chain-of-custody; the chain-of-custody enables a traceability. A variety of new applications are enabled by the blockchain ledger-based supply chain.

19 Claims, 7 Drawing Sheets

(51) Int. Cl.
*G06Q 50/26* (2012.01)
*G06Q 10/10* (2023.01)
*G01G 17/00* (2006.01)
*G06F 16/182* (2019.01)
*G06K 7/14* (2006.01)
*G01N 33/02* (2006.01)
*G06Q 50/02* (2012.01)

(52) U.S. Cl.
CPC ......... *G06F 16/182* (2019.01); *G06K 7/1417* (2013.01); *G06Q 10/10* (2013.01); *G06Q 30/0185* (2013.01); *G06Q 50/02* (2013.01); *G06Q 50/265* (2013.01)

(58) Field of Classification Search
CPC ... G01N 33/025; G06F 16/182; G06K 7/1417
See application file for complete search history.

(56) References Cited

U.S. PATENT DOCUMENTS

| | | |
|---|---|---|
| 9,641,342 B2 | 5/2017 | Sriram et al. |
| 9,747,586 B1 | 8/2017 | Frolov et al. |
| 9,760,574 B1 | 9/2017 | Zhai et al. |
| 9,794,074 B2 | 10/2017 | Toll et al. |
| 9,818,116 B2 | 11/2017 | Caldera |
| 9,849,364 B2 | 12/2017 | Tran et al. |
| 9,852,427 B2 | 12/2017 | Caldera |
| 9,853,819 B2 | 12/2017 | Truu et al. |
| 9,870,508 B1 | 1/2018 | Hodgson et al. |
| 9,876,775 B2 | 1/2018 | Mossbarger |
| 9,888,007 B2 | 2/2018 | Caldera et al. |
| 9,892,460 B1 | 2/2018 | Winklevoss et al. |
| 9,898,782 B1 | 2/2018 | Winklevoss et al. |
| 9,953,281 B2 | 4/2018 | Wiig et al. |
| 9,959,438 B2 | 5/2018 | Uysal et al. |
| 9,965,804 B1 | 5/2018 | Winklevoss et al. |
| 9,965,805 B1 | 5/2018 | Winklevoss et al. |
| 10,002,277 B1 | 6/2018 | Endress et al. |
| 10,002,362 B1 | 6/2018 | Endress et al. |
| 10,002,389 B1 | 6/2018 | Winklevoss et al. |
| 10,022,613 B2 | 7/2018 | Tran et al. |
| 10,025,797 B1 | 7/2018 | Fonss |
| 10,037,533 B2 | 7/2018 | Caldera |
| 10,046,228 B2 | 8/2018 | Tran et al. |
| 10,057,243 B1 | 8/2018 | Kumar et al. |
| 10,068,228 B1 | 9/2018 | Winklevoss et al. |
| 10,084,607 B2 | 9/2018 | Toll et al. |
| 10,102,265 B1 | 10/2018 | Madisetti et al. |
| 10,103,893 B2 | 10/2018 | Kroonmaa et al. |
| 10,115,068 B2 | 10/2018 | Vivier |
| 10,116,765 B2 | 10/2018 | Orbach |
| 10,120,888 B2 | 11/2018 | Almasan et al. |
| 10,121,025 B1 | 11/2018 | Rice |
| 10,127,247 B1 | 11/2018 | Arora et al. |
| 10,162,968 B1 | 12/2018 | Kumar et al. |
| 10,168,693 B2 | 1/2019 | Kingston et al. |
| 10,171,992 B1 | 1/2019 | Viswanathan et al. |
| 10,176,481 B2 | 1/2019 | Aljawhari |
| 10,187,368 B2 | 1/2019 | Way |
| 10,187,369 B2 | 1/2019 | Caldera et al. |
| 10,193,695 B1 | 1/2019 | Endress et al. |
| 10,195,513 B2 | 2/2019 | Tran et al. |
| 10,200,199 B2 | 2/2019 | Truu et al. |
| 10,204,148 B2 | 2/2019 | Madisetti et al. |
| 10,216,948 B2 | 2/2019 | Leporini et al. |
| 10,237,259 B2 | 3/2019 | Ronda et al. |
| 10,250,381 B1 | 4/2019 | Rice |
| 10,250,583 B2 | 4/2019 | Caldera et al. |
| 10,250,708 B1 | 4/2019 | Carver et al. |
| 10,252,145 B2 | 4/2019 | Tran et al. |
| 10,255,342 B2 | 4/2019 | Madisetti et al. |
| 10,255,635 B1 | 4/2019 | Winklevoss et al. |
| 10,261,846 B1 | 4/2019 | Patton |
| 10,262,164 B2 | 4/2019 | Castro et al. |
| 10,262,437 B1 | 4/2019 | Ter Beest |
| 10,268,974 B2 | 4/2019 | Wiig et al. |
| 10,275,627 B2 | 4/2019 | Endress et al. |
| 10,282,741 B2 | 5/2019 | Yu et al. |
| 10,282,762 B2 | 5/2019 | Manning et al. |
| 10,289,631 B2 | 5/2019 | Madisetti et al. |
| 10,299,113 B1 | 5/2019 | Viswanathan et al. |
| 10,302,454 B2 | 5/2019 | Mackie et al. |
| 10,318,546 B2 | 6/2019 | Gupta et al. |
| 10,320,569 B1 | 6/2019 | Wentz et al. |
| 10,325,257 B1 | 6/2019 | Winklevoss et al. |
| 10,333,696 B2 | 6/2019 | Ahmed |
| 10,338,913 B2 | 7/2019 | Franchitti |
| 10,346,428 B2 | 7/2019 | Madhavan et al. |
| 10,346,815 B2 | 7/2019 | Glover et al. |
| 10,354,325 B1 | 7/2019 | Skala et al. |
| 10,356,099 B2 | 7/2019 | Caldera et al. |
| 10,360,128 B2 | 7/2019 | Lingamneni |
| 10,360,449 B2 | 7/2019 | Chandrashekar et al. |
| 10,366,204 B2 | 7/2019 | Tanner et al. |
| 10,373,158 B1 | 8/2019 | James et al. |
| 10,380,682 B2 | 8/2019 | Kundu |
| 10,394,845 B2 | 8/2019 | Madisetti et al. |
| 10,396,997 B2 | 8/2019 | Brady et al. |
| 10,402,607 B2 | 9/2019 | Uysal et al. |
| 10,404,469 B2 | 9/2019 | Madhavan et al. |
| 10,417,217 B2 | 9/2019 | Pierce et al. |
| 10,419,359 B2 | 9/2019 | Way |
| 10,430,898 B2 | 10/2019 | Sun et al. |
| 10,445,538 B2 | 10/2019 | Smith |
| 10,445,643 B2 | 10/2019 | Katz et al. |
| 10,445,698 B2 | 10/2019 | Hunn |
| 10,447,478 B2 | 10/2019 | Gray |
| 10,452,998 B2 | 10/2019 | Cuomo et al. |
| 10,453,233 B2 | 10/2019 | Biradar et al. |
| 10,455,640 B2 | 10/2019 | Nolan et al. |
| 10,456,493 B2 | 10/2019 | Grossman et al. |
| 10,459,946 B2 | 10/2019 | Madisetti et al. |
| 10,466,111 B2 | 11/2019 | Jones et al. |
| 10,467,067 B2 | 11/2019 | Patton et al. |
| 10,467,586 B2 | 11/2019 | Fuller et al. |
| 10,469,248 B2 | 11/2019 | Chalakudi et al. |
| 10,469,250 B2 | 11/2019 | Rady |
| 10,469,263 B2 | 11/2019 | Schukai et al. |
| 10,469,480 B2 | 11/2019 | Kumar et al. |
| 10,474,854 B2 | 11/2019 | Uysal et al. |
| 10,474,855 B2 | 11/2019 | Uysal et al. |
| 10,482,288 B2 | 11/2019 | Rice |
| 10,482,700 B2 | 11/2019 | Soeda |
| 10,489,380 B2 | 11/2019 | Lingamneni |
| 10,489,709 B2 | 11/2019 | Katz et al. |
| 10,491,608 B1 | 11/2019 | Tatge et al. |
| 10,496,923 B2 | 12/2019 | Katz et al. |
| 10,504,178 B2 | 12/2019 | Pierce et al. |
| 10,505,720 B2 | 12/2019 | Li |
| 10,505,920 B2 | 12/2019 | Kumar et al. |
| 10,505,949 B2 | 12/2019 | Zhang |
| 10,509,684 B2 | 12/2019 | Florissi et al. |
| 10,509,891 B2 | 12/2019 | Solow et al. |
| 10,509,927 B2 | 12/2019 | Uysal et al. |
| 10,511,686 B2 | 12/2019 | Orbach |
| 10,511,964 B1 | 12/2019 | Viswanathan et al. |
| 10,515,233 B2 | 12/2019 | Cuomo et al. |
| 10,515,333 B2 | 12/2019 | Vivier |
| 10,520,922 B2 | 12/2019 | Kumar et al. |
| 10,521,446 B2 | 12/2019 | Kanvinde |
| 10,521,806 B2 | 12/2019 | Cantrell et al. |
| 10,528,551 B2 | 1/2020 | Li et al. |
| 10,530,577 B1 | 1/2020 | Pazhoor et al. |
| 10,530,584 B2 * | 1/2020 | Kovach ................ H04L 9/3239 |
| 10,532,268 B2 | 1/2020 | Tran et al. |
| 10,534,362 B2 | 1/2020 | Weldemariam et al. |
| 10,534,923 B2 | 1/2020 | Narasimhan et al. |
| 10,535,063 B2 | 1/2020 | Lingham et al. |
| 10,535,111 B2 | 1/2020 | O'Brien |
| 10,540,342 B2 | 1/2020 | Dasari et al. |
| 10,540,514 B1 | 1/2020 | Winarski |
| 10,540,653 B1 | 1/2020 | James et al. |
| 10,540,654 B1 | 1/2020 | James et al. |

(56) References Cited

U.S. PATENT DOCUMENTS

| | | | |
|---|---|---|---|
| 10,541,807 B1 | 1/2020 | Morimura et al. | |
| 10,541,820 B2 | 1/2020 | Chino et al. | |
| 10,541,821 B2 | 1/2020 | Toll et al. | |
| 10,542,046 B2 | 1/2020 | Katragadda et al. | |
| 10,545,491 B2 | 1/2020 | Kingston et al. | |
| 10,552,381 B2 | 2/2020 | Bastide et al. | |
| 10,552,556 B2 | 2/2020 | Kikinis | |
| 10,552,627 B2 | 2/2020 | Leporini et al. | |
| 10,552,904 B2 | 2/2020 | Wager et al. | |
| 10,552,905 B2 | 2/2020 | Wager et al. | |
| 10,554,388 B2 | 2/2020 | Tang | |
| 10,554,405 B1 | 2/2020 | Endress et al. | |
| 10,555,505 B2 | 2/2020 | Hummer et al. | |
| 10,557,105 B1 | 2/2020 | Tran et al. | |
| 10,559,035 B2 | 2/2020 | Mueller et al. | |
| 10,559,202 B2 | 2/2020 | Yang et al. | |
| 10,560,272 B2 | 2/2020 | Yang et al. | |
| 10,567,320 B2 | 2/2020 | Chalakudi et al. | |
| 10,572,684 B2 | 2/2020 | LaFever et al. | |
| 10,579,643 B2 | 3/2020 | Madisetti et al. | |
| 10,580,100 B2 | 3/2020 | Pierce et al. | |
| 10,581,847 B1* | 3/2020 | Sun | H04L 63/083 |
| 10,592,549 B2 | 3/2020 | Arora et al. | |
| 10,592,985 B2 | 3/2020 | Ford et al. | |
| 10,594,689 B1 | 3/2020 | Weaver et al. | |
| 10,599,491 B2 | 3/2020 | Patton | |
| 10,600,006 B1 | 3/2020 | Wang et al. | |
| 10,600,050 B1 | 3/2020 | Anton et al. | |
| 10,601,907 B2 | 3/2020 | Hernandez et al. | |
| 10,607,484 B2 | 3/2020 | Yang et al. | |
| 10,608,825 B2 | 3/2020 | Berg | |
| 10,621,233 B2 | 4/2020 | Saxena et al. | |
| 10,621,510 B2 | 4/2020 | Saxena et al. | |
| 10,621,511 B2 | 4/2020 | Saxena et al. | |
| 10,621,674 B2 | 4/2020 | Jones et al. | |
| 10,623,173 B1 | 4/2020 | Geng et al. | |
| 10,627,451 B2 | 4/2020 | Karner et al. | |
| 10,628,491 B2 | 4/2020 | Saxena et al. | |
| 10,628,828 B2 | 4/2020 | Caldera | |
| 10,630,468 B1 | 4/2020 | Wang et al. | |
| 10,630,769 B2 | 4/2020 | Carver et al. | |
| 10,635,959 B2 | 4/2020 | Guo | |
| 10,637,669 B2 | 4/2020 | Johnson et al. | |
| 10,642,643 B2 | 5/2020 | Qiu | |
| 10,642,967 B2 | 5/2020 | Balaraman et al. | |
| 10,643,203 B2 | 5/2020 | Furche et al. | |
| 10,643,288 B2 | 5/2020 | Orsini et al. | |
| 10,649,429 B2 | 5/2020 | Orsini | |
| 10,650,023 B2 | 5/2020 | Montgomery-Recht et al. | |
| 10,650,376 B1 | 5/2020 | Winklevoss et al. | |
| 10,652,171 B2 | 5/2020 | Basheer et al. | |
| 10,652,228 B2 | 5/2020 | Way | |
| 10,657,151 B2 | 5/2020 | Qiu | |
| 10,657,261 B2 | 5/2020 | Kumar et al. | |
| 10,657,566 B2 | 5/2020 | Manning et al. | |
| 10,657,595 B2 | 5/2020 | Jong et al. | |
| 10,659,217 B2 | 5/2020 | Ramasamy et al. | |
| 10,661,594 B2 | 5/2020 | Trexler et al. | |
| 10,664,305 B1 | 5/2020 | Qiu | |
| 10,664,485 B2 | 5/2020 | Zhang et al. | |
| 10,673,617 B1 | 6/2020 | Antoniou et al. | |
| 10,673,620 B2 | 6/2020 | Nuzzi | |
| 10,673,958 B1 | 6/2020 | Wylie et al. | |
| 10,673,982 B2 | 6/2020 | Acosta et al. | |
| 10,676,219 B2 | 6/2020 | Colson et al. | |
| 10,677,723 B2 | 6/2020 | Ditterich | |
| 10,678,866 B1 | 6/2020 | Ranganathan et al. | |
| 10,679,128 B2 | 6/2020 | Katz et al. | |
| 10,679,223 B2 | 6/2020 | Endress et al. | |
| 10,681,049 B2 | 6/2020 | Jeuk et al. | |
| 10,685,323 B2 | 6/2020 | Fuller et al. | |
| 10,691,674 B2 | 6/2020 | Leong et al. | |
| 10,692,086 B2 | 6/2020 | Leong et al. | |
| 10,699,240 B2 | 6/2020 | Kibbey et al. | |
| 10,715,330 B1* | 7/2020 | Govekar | H04L 9/088 |
| 11,100,128 B2 | 8/2021 | Vijayaraghavan et al. | |
| 11,138,396 B2 | 10/2021 | Uysal et al. | |
| 11,139,954 B2* | 10/2021 | Mercuri | G06F 21/602 |
| 11,210,625 B2 | 12/2021 | Kibbey et al. | |
| 11,244,125 B2 | 2/2022 | Uysal et al. | |
| 11,250,394 B1* | 2/2022 | Madisetti | G06Q 20/3825 |
| 11,281,955 B2 | 3/2022 | Saenz et al. | |
| 11,308,051 B1 | 4/2022 | Mayberry et al. | |
| 11,416,725 B1 | 8/2022 | Henrichon, Jr. et al. | |
| 2005/0061878 A1* | 3/2005 | Barenburg | G06K 19/06046 235/385 |
| 2006/0106718 A1* | 5/2006 | Spellman | H04L 9/3247 705/50 |
| 2009/0198541 A1* | 8/2009 | Dolan | G06Q 10/087 705/29 |
| 2013/0262330 A1* | 10/2013 | Sannier | G06Q 10/08 705/318 |
| 2014/0201094 A1* | 7/2014 | Herrington | G06V 20/80 705/317 |
| 2015/0026214 A1* | 1/2015 | Monahan | G06Q 50/265 707/782 |
| 2015/0262347 A1* | 9/2015 | Duerksen | G07D 7/20 382/182 |
| 2015/0278757 A1* | 10/2015 | Walden | G06Q 10/0838 235/376 |
| 2016/0164884 A1* | 6/2016 | Sriram | G06Q 10/0833 705/51 |
| 2016/0217436 A1* | 7/2016 | Brama | G06Q 20/10 |
| 2016/0307381 A1* | 10/2016 | Siebels | G07C 9/28 |
| 2016/0358186 A1* | 12/2016 | Radocchia | H04W 12/02 |
| 2017/0046709 A1* | 2/2017 | Lee | G06Q 20/065 |
| 2017/0140388 A1* | 5/2017 | Thorne | G06Q 50/18 |
| 2017/0230189 A1* | 8/2017 | Toll | H04L 9/0618 |
| 2017/0243159 A1* | 8/2017 | Hurst | G06Q 10/0833 |
| 2017/0243233 A1* | 8/2017 | Land | G06F 21/73 |
| 2017/0262862 A1* | 9/2017 | Aljawhari | G06F 16/242 |
| 2017/0331896 A1* | 11/2017 | Holloway | H04L 67/104 |
| 2018/0039997 A1* | 2/2018 | Nilsson | G06K 7/10 |
| 2018/0108024 A1* | 4/2018 | Greco | H04W 4/029 |
| 2018/0114168 A1* | 4/2018 | Ryan | G06Q 10/08 |
| 2018/0130050 A1* | 5/2018 | Taylor | H04L 9/3236 |
| 2018/0174094 A1* | 6/2018 | Ren | G06F 21/64 |
| 2018/0189528 A1* | 7/2018 | Hanis | G06Q 30/0185 |
| 2018/0191714 A1* | 7/2018 | Jentzsch | H04L 9/3247 |
| 2018/0276600 A1* | 9/2018 | Fuller | H04L 9/3236 |
| 2018/0284093 A1* | 10/2018 | Brown | H04W 4/38 |
| 2018/0285810 A1* | 10/2018 | Ramachandran | G06Q 10/087 |
| 2018/0308046 A1* | 10/2018 | Schutt | G06Q 50/02 |
| 2018/0336515 A1* | 11/2018 | Mehring | H04L 9/0637 |
| 2018/0365633 A1* | 12/2018 | Hanis | G06Q 10/0833 |
| 2018/0374037 A1* | 12/2018 | Nazzari | G09C 5/00 |
| 2019/0002147 A1* | 1/2019 | Scarabelli | B65B 55/103 |
| 2019/0026685 A1* | 1/2019 | Chappell | G06Q 10/087 |
| 2019/0114584 A1* | 4/2019 | Toohey | G06Q 10/083 |
| 2019/0120728 A1* | 4/2019 | Schindler, III | G01N 1/02 |
| 2019/0122086 A1* | 4/2019 | Basu | H04L 67/1042 |
| 2019/0188732 A1* | 6/2019 | Hill | G06V 20/10 |
| 2019/0195852 A1* | 6/2019 | Bryant, Jr. | G01N 33/0098 |
| 2019/0205894 A1* | 7/2019 | Gonzales, Jr. | G06F 21/6245 |
| 2019/0241982 A1* | 8/2019 | Hogan | C12Q 1/68 |
| 2019/0258961 A1* | 8/2019 | Nguyen | G06Q 20/401 |
| 2019/0266612 A1* | 8/2019 | McHale | H04L 9/0866 |
| 2019/0311108 A1* | 10/2019 | Achkir | G06F 21/57 |
| 2019/0331702 A1* | 10/2019 | Menhardt | G01N 35/00613 |
| 2019/0342035 A1* | 11/2019 | Kube | H04L 9/3239 |
| 2019/0392457 A1* | 12/2019 | Kuntagod | H04L 67/12 |
| 2019/0394179 A1* | 12/2019 | Androulaki | H04L 9/0822 |
| 2020/0019931 A1* | 1/2020 | Prabhakar | H04L 63/102 |
| 2020/0034876 A1* | 1/2020 | Soundararajan | H04L 9/0637 |
| 2020/0053952 A1* | 2/2020 | Rabby | H04L 9/0643 |
| 2020/0057980 A1* | 2/2020 | Perkowitz | H04L 9/50 |
| 2020/0059363 A1* | 2/2020 | Lobo | H04L 9/0637 |
| 2020/0065761 A1* | 2/2020 | Tatchell | G06Q 20/3825 |
| 2020/0074478 A1* | 3/2020 | Peters | G06Q 10/0831 |
| 2020/0136799 A1* | 4/2020 | Smith | H04L 63/00 |
| 2020/0160354 A1* | 5/2020 | Howard | G06K 19/06028 |
| 2020/0177386 A1* | 6/2020 | Mahmood | G16H 20/17 |
| 2020/0184153 A1* | 6/2020 | Bongartz | A01G 9/249 |

(56) References Cited

U.S. PATENT DOCUMENTS

| | | | | |
|---|---|---|---|---|
| 2020/0211005 A1* | 7/2020 | Bodorik | ............. | G06Q 20/3829 |
| 2020/0219034 A1* | 7/2020 | Randhawa | ....... | G06Q 10/06395 |
| 2020/0259658 A1* | 8/2020 | Libsch | .................... | G06F 21/72 |
| 2020/0265446 A1* | 8/2020 | Vargas | ................. | G06Q 10/087 |
| 2020/0279211 A1* | 9/2020 | Gillett | .................. | G06K 7/1413 |
| 2020/0279273 A1* | 9/2020 | Meszaros | ............... | G06Q 50/28 |
| 2020/0294032 A1* | 9/2020 | Cheng | ................. | H04L 63/0861 |
| 2020/0301997 A1* | 9/2020 | Smith | ..................... | G06F 17/15 |
| 2020/0351094 A1* | 11/2020 | Canterbury | ........... | H04L 9/0637 |
| 2020/0359550 A1* | 11/2020 | Tran | ...................... | G06F 3/0346 |
| 2022/0277261 A1* | 9/2022 | Stollman | ................ | G06Q 10/08 |

FOREIGN PATENT DOCUMENTS

| | | | | | |
|---|---|---|---|---|---|
| WO | WO-2013052990 A1 * | 4/2013 | | ........... | G06F 16/284 |
| WO | WO-2017027648 A1 * | 2/2017 | | ............. | G06Q 10/08 |
| WO | WO-2019005104 A1 * | 1/2019 | | ............. | G06F 16/258 |
| WO | WO-2020084446 A1 * | 4/2020 | | ........... | G06F 16/245 |

OTHER PUBLICATIONS

A. Shahid, A. Almogren, N. Javaid, F. A. Al-Zahrani, M. Zuair and M. Alam, "Blockchain-Based Agri-Food Supply Chain: A Complete Solution," in IEEE Access, vol. 8, pp. 69230-69243, 2020, doi: 10.1109/ACCESS.2020.2986257. (Year: 2020).*

Hawaii Department of Health Sets up Medical Marijuana Seed-to-Sale Tracking, Traceability System. Coventry: Normans Media Ltd, 2016. Print. (Year: 2016).*

Downie, G., & Parker, D., Parker. (2020). Blockchain technology: The missing link in services management? part II A. Management Services, 64(1), 41-47. Retrieved from https://www.proquest.com/trade-journals/blockchain-technology-missing-link-services/docview/2388005626/se-2 (Year: 2020).*

Chang, Yanling, Eleftherios Iakovou, and Weidong Shi. "Blockchain in global supply chains and cross border trade: a critical synthesis of the state-of-the-art, challenges and opportunities." International Journal of Production Research 58.7 (2020): 2082-2099. (Year: 2020).*

* cited by examiner

METHODS AND APPARATUS FOR PERFORMING AGRICULTURAL TRANSACTIONS

PRIORITY AND RELATED

This application claims the benefit of priority to U.S. Provisional Patent Application Ser. No. 62/981,271 filed Feb. 25, 2020 and entitled "METHODS AND APPARATUS FOR PERFORMING AGRICULTURAL TRANSACTIONS", which is incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

TECHNICAL FIELD

This disclosure relates generally to the field of agricultural logistics. More particularly, the present disclosure relates to systems, computer programs, devices, and methods for transacting, recording, validating and/or verifying agricultural products.

DESCRIPTION OF RELATED TECHNOLOGY

Advances in logistics and supply chain management for agricultural products (e.g., crops, crop products, livestock, livestock products, etc.) have enabled industrial farming in the U.S. (and abroad) at unprecedented scales. The modern supply chain inexpensively delivers a myriad of agricultural products (fresh and processed) from individual farms to consumer households, year-round. Notably, the efficiencies of the modern agricultural supply chain can be directly traced to: (i) massive economies of scale, and (ii) the division of labor.

As but one such example, tropical fruits that were originally grown in Florida can be delivered (while still fresh) in the middle of winter, to households in Oregon. For instance, an individual orange farmer and a pineapple farmer can independently deliver their products to a nearby distribution center in Florida. The distribution center combines the oranges and pineapples (along with other agricultural products) for cost effective delivery to Oregon markets. Local stores in Oregon can cater to their specific consumer tastes (which may include tropical fruits). Each participant in the supply chain can focus on optimizing their costs and overhead for a small set of tasks.

While the modern agricultural supply chain provides many benefits, recent changes in consumer markets have introduced novel demands that cannot be addressed within the existing agricultural supply chain framework. To these ends, improvements in transacting, recording, validating and/or verifying agricultural products are needed.

SUMMARY

The present disclosure addresses the foregoing needs by disclosing, inter alia, methods, devices, systems, and computer programs for transacting, recording, validating and/or verifying agricultural products.

In one aspect, a method for chain-of-custody based enforcement is disclosed. In one embodiment, the method includes: reading physical indicia of a bailment to retrieve a set of records from a distributed ledger associated with the bailment; verifying a custody record of the set of records for the bailment; measuring a physical characteristic of the bailment; validating that the physical characteristic matches a previously recorded measurement record of the set of records for the bailment; and adding a new record to the distributed ledger.

In one variant, reading the physical indicia of the bailment comprises scanning a quick response code printed on a physically intact tamper-proof label, where the set of records are retrieved from a blockchain-based ledger based on the quick response code.

In one variant, verifying the custody record comprises determining that an identity of a person in possession of the bailment matches the custody record.

In one variant, verifying the custody record comprises determining that a current location of the bailment matches the custody record.

In one variant, verifying the custody record comprises determining that a previous location of the bailment matches the custody record.

In one variant, measuring the physical characteristic of the bailment comprises measuring a dry weight and the previously recorded measurement record comprises a previously measured dry weight.

In one variant, measuring the physical characteristic of the bailment comprises measuring a chemical composition and where the previously recorded measurement record comprises a previously chemical composition.

In one aspect, an apparatus for chain-of-custody based enforcement is disclosed. In one embodiment, the apparatus includes: a reader configured to read physical indicia; a network interface configured to communicate with a distributed ledger; a processor; and a non-transitory computer-readable medium. In one exemplary embodiment, the non-transitory computer-readable medium includes one or more instructions which when executed by the processor, cause the apparatus to: read the physical indicia of a bailment; retrieve a set of records associated with the physical indicia from the distributed ledger associated with the bailment; and report the bailment for regulatory response when the set of records does not match the bailment.

In one variant, the apparatus further includes a geospatial subsystem configured to determine a current location of the bailment and the set of records includes a custody record that identifies an authorized area.

In one variant, the apparatus further includes logic configured to identify a person in possession of the bailment and the set of records includes a custody record that identifies an authorized bailee.

In one variant, the apparatus includes logic configured to identify a source or destination of the bailment; and the set of records includes a consignment record that identifies at least one of a consignor and a consignee.

In one variant, the apparatus includes a sensor configured to measure a physical characteristic of the bailment and the set of records includes a previously measured physical characteristic of the bailment. In one such variant, the sensor measures a dry weight of the bailment. In one such variant, the sensor measures a chemical composition of the bailment.

In one aspect, an apparatus configured to record a chain-of-custody for a bailment is disclosed. In one embodiment, the apparatus includes: a network interface configured to communicate with a community of independent devices; a processor; and a non-transitory computer-readable medium. In one exemplary embodiment, the non-transitory computer-readable medium includes one or more instructions which when executed by the processor, cause the apparatus to: consensually store a distributed ledger with the community of independent devices; generate a code for a consignment; associate a set of records for the consignment with the code within the distributed ledger; and responsive to a query comprising the code, retrieve at least one record of the set of records.

In one variant, the consignment is associated with a consignor entity and a consignee entity.

In one variant, the one or more instructions when executed by the processor, further cause the apparatus to: generate a first bailment record associated with the consignment; where the first bailment record identifies a first bailor in actual custody of the bailment; where the first bailment record identifies a set of responsibilities for the bailment that are assigned to a bailee when the bailment is intact; and wherein the at least one record comprises the first bailment record. In one such variant, the at least one record comprises at least a second bailment record that identifies a second bailor in constructive custody of the bailment. In some such cases, the one or more instructions when executed by the processor, further cause the apparatus to: responsive to a first broken bulk event occurrence, convert a first responsibility for the bailment to the first bailor. Additionally, the one or more instructions when executed by the processor, may further cause the apparatus to responsive to a second broken bulk event occurrence, convert a second responsibility for the bailment to the second bailor.

More broadly, systems, methods, and apparatus for an exemplary testing and permitting process are disclosed.

Additionally, systems, methods, and apparatus for chain-of-custody based enforcement are disclosed.

Furthermore, systems, methods, and apparatus for transferring bailments are disclosed.

Still additionally, systems, methods, and apparatus for monitoring consignment via a distributed ledger are disclosed.

Other features and advantages of the present disclosure will immediately be recognized by persons of ordinary skill in the art with reference to the attached drawings and detailed description of exemplary embodiments as given below.

Figure 1:
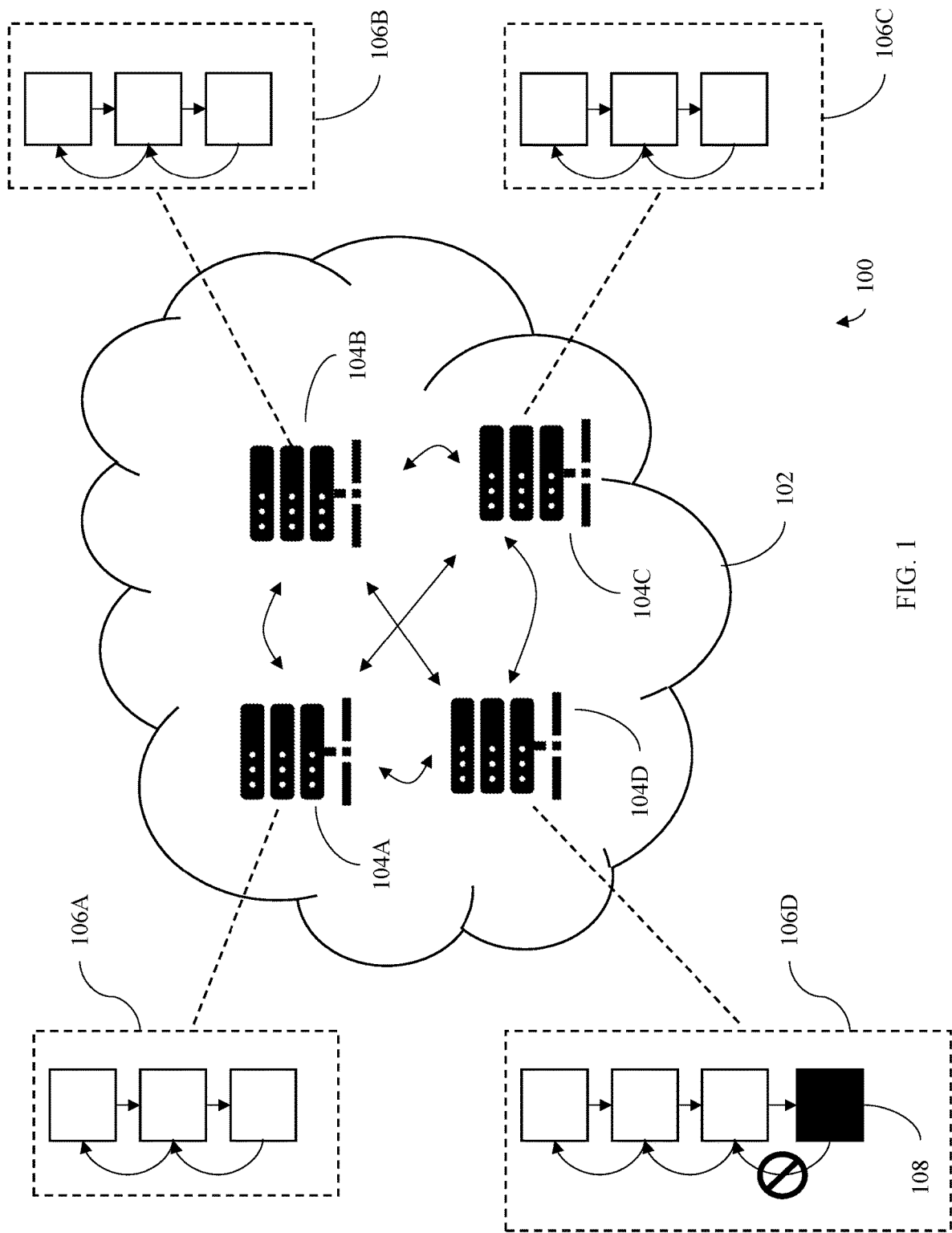
FIG. 1 is a logical block diagram of a blockchain network, useful for explaining existing blockchain operation.

All Figures© The inventor Mark R. Coast. 2019-2020, All rights reserved.

DETAILED DESCRIPTION

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without departing from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

Blockchains and Cryptocurrencies

As a brief aside, a "currency" serves as a medium of exchange for goods or services. Unlike physical currencies which represent value with physical objects (such as paper bills and coins), virtualized currencies represent value as digital data. Physical currencies can be manufactured with counterfeiting countermeasures (e.g., special inks, materials, etc.); similarly, so-called "cryptocurrencies" are virtualized currencies that use cryptography to prevent counterfeiting and double spending.

Blockchains are one example of a cryptographic technique that is used within many cryptocurrencies. A blockchain is a digital ledger of virtual transactions. Specifically, each virtual transaction is recorded as a "block"; the block also contains a cryptographic hash of its previous block, a timestamp, and transaction data. The digital ledger is the ordered chain of blocks (e.g., the "blockchain"). Notably, the cryptographic hash is a mathematical algorithm that generates a hash value of fixed size from data of arbitrary size; the cryptographic hash is a one-way function (i.e., computationally simple to calculate the hash value but much more difficult, if not impossible, to reverse-lookup the data that corresponded to the hash value.) The one-way nature of the cryptographic hash and the linked nature of the blockchain ensures that malicious attackers cannot practically attack the blockchain by replacing any single block (all downstream blocks must be re-calculated for the blockchain to be valid; for a sufficiently large blockchain, the processing complexity is impractical).

FIG. 1 is a logical block diagram of a blockchain network 100, useful for explaining existing blockchain operation. As therein, the blockchain network 100 includes a community 102 of independent parties 104A, 104B, 104C, 104D. Each of the parties stores its own copy of a distributed ledger 106A, 106B, 106C, 106D; the distributed ledgers provide an independently accessible historic record of transactions. Typically, the community 102 may be open to the public, but private and/or semi-private implementations also exist. Unlike centralized systems which have a single root of trust, the blockchain network relies on self-interest of the independent parties to preserve the integrity of the distributed ledger.

Blockchain ledgers counteract the problem of double spending cryptocurrencies and other digital assets (e.g., a digital file can be infinitely reproduced and re-spent). Double spending is unique to digital assets because the cost to copy a digital file is negligible (effectively zero) compared to the value that the digital file represents. More directly, blockchain technologies are not merely an extension of well-known business practices from the pre-Internet world that are performed on the Internet. Instead, blockchain technologies are necessarily rooted in computer technology in order to overcome the "infinite reproducibility" problem specifically arising in the realm of computer networks. Notably, the blockchain ledger is not intrinsically valuable and can be copied infinitely. Instead, the blockchain ledger stores a record of transactions of value and an associated proof-of-work; in order to add a "valid" record to the blockchain, computational work must be performed (e.g., a random cryptographic problem.) The "proof-of-work" is a digital representation of entropy that can be easily verified. In other words, proof-of-work transforms a random computation into verifiable entropy (a different state) e.g., the electronic signal (proof) represents a physical parameter (work expended). While the foregoing discussion is presented in the context of "proof-of-work" blockchains, other proof mechanisms may be substituted with equal success given the contents of the present disclosure; examples of such mechanisms include e.g., "proof-of-stake", "proof-of-space", "proof-of-connectivity", etc.

Consider the illustrated scenario where one of the servers 104D attempts to add block 108 without calculating the requisite proof-of-work. The other servers 104A, 104B, 104C check the proposed block 108 against their individual copies of the ledger 106A, 106B, 106C and easily determine that the newly proposed block 108 does not have a correctly calculated proof-of-work. The community updates their copies of the distributed ledger when a majority consensus is reached (e.g., in this case, block 108 is rejected). In some cases, attempts to defraud the community may result in censure (e.g., warning, suspension, and/or expulsion.) While the illustrated example is presented in the context of a block addition, the concept may be broadly extended to any distributed ledger modification (e.g., changes to previous blocks, etc.)

More directly, blockchains and distributed ledgers were designed for situations where participants do not trust one another; each participant verifies and audits transactions using the one-way cryptographic hash in isolation from the other participants. A consensus voting mechanism among the participants resolves ledger differences. The distributed and decentralized nature of the participants ensures that a malicious party cannot counterfeit the ledger by attacking any single participant. Simultaneously fooling a majority of the network participants (also commonly referred to as a "51% attack") is exponentially complex as a function of network size; for a large number of independent parties it is infeasible.

Incipient research is directed to extending blockchain technologies to applications beyond cryptocurrencies; one such field is physical asset management. Physical assets do not suffer from infinite reproducibility, however other aspects are similar to digital assets. For example, certain goods may have intangible value (brand value, consumer good faith, patent protection, etc.) that can be counterfeited or replicated and sold at substantial profit. Existing supply chain blockchains attempt to e.g., assign a digital signature to a physical asset. For example, a physical object may be marked with an anti-counterfeit product marking. The product marking includes a pointer indicating the block of a blockchain where the product details may be obtained. The product details may be used to identify e.g., a designation of origin, manufacturer, or another similar characteristic. However, counterfeit detection applications have a single arbiter of truth i.e., the original manufacturer. Such blockchain applications do not provide either decentralization or independent verification. Additionally, the distributed and decentralized nature of blockchain networks requires much more transactional overhead than more traditional centralized systems. Thus, such supply chain blockchains are usually nothing more than cumbersome databases.

Illicit Drug Trade and Enforcement

In a wholly separate but important tangent, unlike "white market" (licit) trade which operates lawfully, "black market" (illicit) trade is prohibited by law and seeks to subvert and avoid government and regulatory oversight. Transactions and contracts are often self-policed and enforced via extra-legal infrastructures (e.g., criminal organizations). In criminal organizations, individuals are often sparsely connected and may lack knowledge of other participants; in many situations, opacity is necessary to thwart law enforcement. For example, a marijuana farm often has little visibility into its distribution network to street dealers, and vice versa. As a related issue, the clandestine nature of the black market often requires that transactions are anonymous; typically, cash, barter, or similarly untraceable medium of exchange is used.

Existing law enforcement networks often must use a variety of different techniques that differ from white market commercial regulation. For example, licit businesses may be required to apply for permits and licenses; part of the permitting/licensing process may entail routine inspection, compliance with regulatory codes, etc. Businesses are significantly incentivized to maintain transparent accounting and comply with regulations; failure to do so may result in harsh penalties (including business closure). In contrast, illicit businesses often take extravagant measures to avoid law enforcement; goods may need to be smuggled and/or circuitously trafficked. Illicit proceeds are "laundered" and commingled with licit proceeds. These additional costs can be directly added the prices of goods; thus, smugglers are price insensitive. As a result, law enforcement and smugglers escalate measure for countermeasure in a continuous "arms race."

Differences between commercial regulation and law enforcement have created very different institutional assumptions, structures, and protocols. Commercial regulation typically balances a variety of factors: e.g., consumer protection, regulatory overhead, market competition, tax revenue, public policy, etc. For example, inspecting food products for contaminants (e.g., *E. coli, Salmonella*, etc.) is necessary to protect consumers; however, excessive inspection requirements may be commercially counterproductive. Industry advocates, regulatory bodies, and consumer groups often must work together to find reasonable compromises. In contrast, law enforcement has a singular purpose, and may go to extraordinary lengths to stop criminal activity. Contraband is price insensitive; this can result in well-funded criminal enterprises with the power and the means to rival sophisticated government agencies. Police officers routinely police public areas, covertly monitor individuals, and may force access onto private premises. Additionally, specialized law enforcement entities are equipped with specialized capabilities and/or tools. As but one such example, the Financial Crimes Enforcement Network (FinCEN) monitors banking activity to flag suspicious financial activity and/or freeze financial assets and financial institutions that are implicated in illegal activities.

The Legalization of Hemp, as Distinguished from Marijuana

The 2018 Farm Act[1] rescinded industrial hemp from Schedule I of the Controlled Substances Act (CSA). The new law designated the US Department of Agriculture (USDA) as the lead Federal agency, under National Institute of Food and Agriculture (NIFA) and addressed Strategic Goal 3: Promote American Agriculture Products and Strategic Goal 7: Exports and Provide All Americans Access to a Safe, Nutritious, and Secure Food Supply. Although industrial hemp has a variety of uses ranging from concrete, insulation, paper products, and rope; the Government's biggest concern is the ingestion of specifically two chemicals which occur naturally in the *Cannabis Sativa* L plant. One chemical is tetrahydrocannabinol (THC) which remains a controlled substance on the CSA and is regulated by the Drug Enforcement Administration (DEA). The other chemical is cannabidiol (CBD). CBD has seen an explosion in popularity and in creation of hundreds of products including ingestible food additives and medicinal research products. In fact, hemp may be more valuable than marijuana because refined and purified CBD isolate is more valuable than THC.

[1] Agriculture Improvement Act of 2018 (commonly known as the 2018 Farm Bill), H.R.2, 115th Congress of the United States. Enacted Dec. 20, 2018.

Currently (circa 2019-2020), the U.S. Food and Drug Administration (FDA) defines "hemp" as the plant *Cannabis Sativa* L. and any part of that plant, including the seeds thereof and all derivatives, extracts, cannabinoids, isomers, acids, salts, and salts of isomers, whether growing or not, with a delta-9 tetrahydrocannabinol [delta-9 THC] concentration of not more than 0.3 percent on a dry weight basis. Existing domestic regulatory and statutory definitions remain in flux at the time of this filing and may change over time; furthermore, other juristic entities may independently define hemp or its derivatives differently. Thus, artisans of ordinary skill in the related arts given the contents of the present disclosure will readily acknowledge that other definitions may be substituted with equal success, the foregoing being purely illustrative.

The enactment of the 2018 Farm Bill legalized national cultivation of industrial hemp and created a hybrid of State, Tribal, Territory, and Federal regulations to administer the new agricultural commodity. No less than a half a dozen Federal stakeholders, such as the USDA, FDA, DEA, Office of Comptroller and Currency (OCC), Financial Crimes Enforcement Network (FinCEN), and Internal Revenue Service (IRS). Currently, 46 States have passed legislation regarding the cultivation of industrial hemp.[2] Similarly, dozens of tribal nations and U.S. territories, such as Puerto Rico, have passed, or are pending legislation, regarding industrial hemp cultivation. The USDA, as the lead Federal agency is expected to coordinate and collaborate with no less than 60 Federal agencies, States, Tribal nations, and U.S. territories to ensure regulatory commodity compliance, food safety, and food security.

[2] Retrieved from www.votehemp.com 501(c)(4) non-profit website on Aug. 29, 2019.

This new law also mandated a series of compliance elements throughout the lifecycle of the plant and its by-products. The compliance mechanisms include permits, chemical tests of plants and products, reporting requirements, background checks of new employees, and even verification of domestic crop, or lot, size and location. Essentially, multiple agencies within the US Government are tasked with oversight of the cultivation of industrial hemp, cultivators, processors, manufacturers, and retailers. This is an enormous undertaking. Although the new law requires many regulatory mechanisms, which create unique challenges, it also presents tremendous opportunities to advance the agricultural industry as a whole.

Further complicating matters, the myriad of aforementioned Federal, State, Tribal, and private party agencies must coordinate their efforts, but often cannot share information. For example, private farmers must be able to identify, collaborate, and/or report other parties (e.g., other farmers, distributors and/or marketplaces), however they should not have access to e.g., financial transactions, tax records, etc. of their business partners. Similarly, interstate banks should be able to loan money to small hemp farmers without worrying about running afoul of drug trafficking and/or money laundering enforcement (e.g., FinCEN). In other words, the burgeoning applications for hemp as a licit agricultural product require changes to the agricultural supply chain that are novel and unique. Specifically, the hemp industry requires multiple parties to cooperate in real-time, with shared information, in a decentralized manner across a variety of different regulatory regimes.

Example Operation

Existing "field tests" for marijuana only detect the presence (not percentage) of THC. Specifically, field tests are based on sensitive chemical reagents. Samples of suspected material are sealed with glass ampules of reagents. The ampules are broken to mix the reagents with the test material. The reagent will visibly indicate (turn purple), if THC is present to within one part per million (0.000001%). Unfortunately, hemp can have up to three parts per thousand of THC (0.3%), thus existing field tests incorrectly flag hemp as marijuana. More directly, while hemp is a legalized agricultural product it remains indistinguishable from marijuana for law enforcement officers (LEOs).

While laboratory tests can be used to identify a specific percentage of THC, such tests require specialized lab equipment and trained technicians. Even assuming arguendo that THC percentage could be determined from field tests, existing law enforcement techniques are ill-suited for commercial regulation and vice versa. Due to differences in the regulatory environments for hemp, each territory may have their own requirements for THC percentages (e.g., some States have legalized marijuana and may not adequately check for THC percentage). Impounding hemp shipments for LEOs to spot check every shipment crossing state lines is not commercially practical. Additionally, predictability and reliability are highly desired in commercial supply chain management but could be easily circumvented by smugglers.

Furthermore, many parties cannot share data and/or do not trust one another; for example, private parties may remain suspicious of law enforcement. As previously noted, the aforementioned Federal, State, Tribal, and private party agencies must coordinate their efforts, but often cannot share information to effectively corroborate disparate information. This is a particular problem when it comes to regulatory compliance. For example, cultivators, processors, refiners, retailers, can comply with all the regulations of the state and federal agencies, but have no manner or method to demonstrate their demonstrate compliance across multiple jurisdictions. The lack of trust, nor methodology to verify compliance, only compounds a serious problem which routinely results in unwarranted arrests and seizures of agriculture commodities. The typical outcome is the unnecessary destruction of a perishable commodity while the seizing law enforcement agency's laboratory analyzes the commodity for contraband.

In view of the foregoing, the following disclosed embodiments provide systems, apparatus, methods and storage media that transact, record, and validate/verify agricultural products via a blockchain-based ledger. Each entity within an agricultural product supply chain has access to a limited subset of capabilities based on privilege and/or access restrictions. In one specific implementation, the privileges and/or access restrictions are formalized as a set of smart contracts.

As used herein, the term "smart contract" refers to a protocol that formalizes a contractual transaction for software execution. Smart contracts record, facilitate, validate, verify, enforce negotiation (e.g., a contractual offer, acceptance, and/or consideration etc.) and/or evaluate performance of a contract within software (with limited or no human intervention). Notably, the exemplary smart contracts described herein are not merely software implementations of well-known mental processes or longstanding commercial practices. Culpability is a significant consideration for the hemp industry due to the potential for abuse in marijuana smuggling. Smart contracts enable commercial transactions without transferring culpability between human participants. As used herein, culpability refers to the measure or degree to which a human may be held liable for their conduct.

As used herein, the terms "blockchain-based", "blockchain-based ledger", "blockchain-based supply chain", etc. refer to a blockchain data structure that is primarily used to record a chain-of-custody of physical goods. More directly, unlike cryptocurrencies and other blockchain applications which are focused on virtual assets in the digital domain, the agricultural blockchain-based supply chain described herein uses blockchains to immutably record transactions of physical goods between participants in the real world.

Figure 2A:
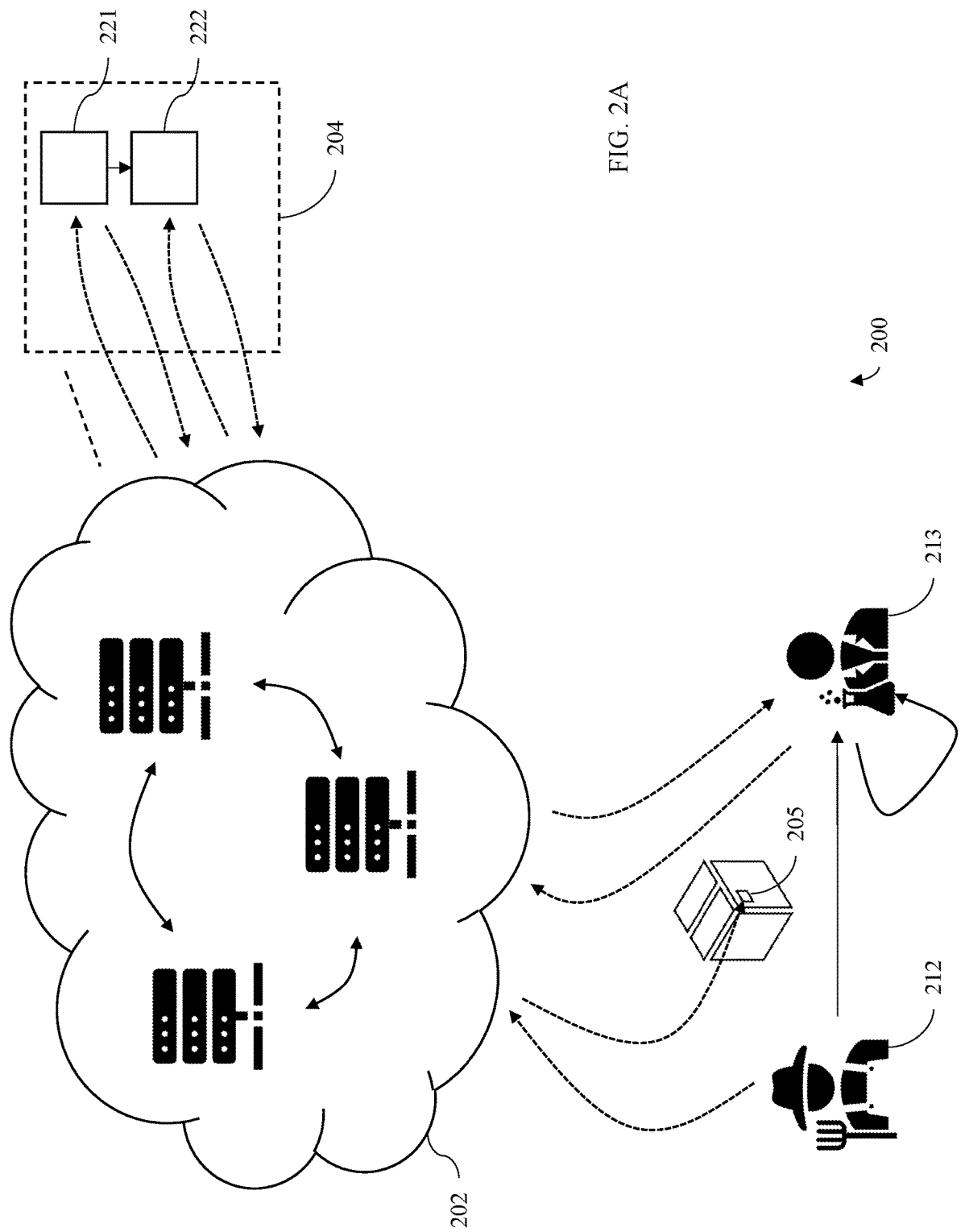
FIG. 2A is a logical block diagram of an exemplary testing and permitting process, in accordance with the various principles described herein.

FIG. 2A is a logical block diagram of an exemplary testing and permitting process 200. As shown therein, the illustrated system 200 includes a decentralized network of servers 202 that store distributed copies of an agricultural blockchain-based ledger 204 of transactions. FIG. 2A depicts a cultivator/farmer 212 and a DEA registered chemist/technician 213.

In one exemplary embodiment, the inspector/cultivator/farmer 212 gathers in-ground samples corresponding to different hemp plants of a lot (geospatially identified crop locations). Each in-ground sample has a unique sample number/identifier; a unique lot identifier is generated by combining all the sample numbers/identifiers for the lot. The unique number/identifier is stored in a blockchain record 221 and assigned a unique Quick Response (QR) Code; the QR code is printed on a tamper-proof self-adhesive sealing label 205. Once applied, tamper-proof labels cannot be removed without detection (the labels disintegrate with any removal attempt), thus establishing (indicative of) a chain-of-custody.

The sealed package 205 is sent to a DEA registered chemical testing laboratory 213 for chemical analysis. The results of the chemical analysis, including THC percentage in the sample, are uploaded to the blockchain 222 as an official DEA recognized analysis. If the test determines that the sample contains 0.3% or less THC, then the sample is hemp, and the cultivator 212 may be permitted/licensed (or obtain permits/licenses) to ship subsequently harvested biomass from the lot. If the sample is above 0.3% the crop will undergo State remediation process.

Figure 2B:
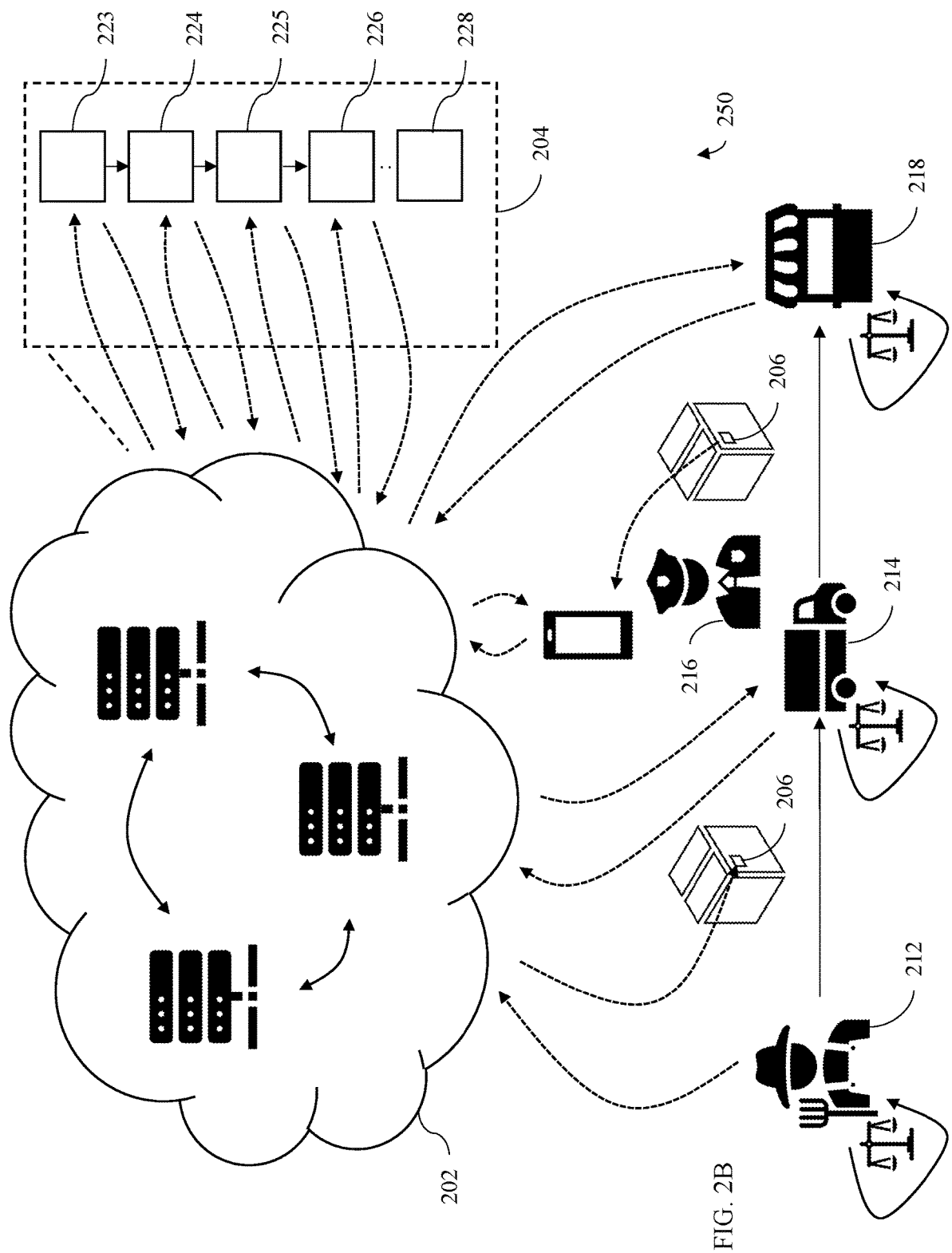
FIG. 2B is an exemplary logical block diagram of one exemplary agricultural blockchain supply chain system, in accordance with the various principles described herein.

Referring now to FIG. 2B, a logical block diagram of the exemplary agricultural blockchain supply chain system 250 is shown. The supply chain system 250 includes a permitted cultivator/farmer 212, a transporter 214, and retailer 218 that each access the agricultural blockchain-based ledger at different points and with different privileges within the supply chain. A law enforcement officer (LEO) 216 may inspect the supply chain at any point.

Initially, harvested biomass is processed for shipment; for instance, the permitted cultivator/farmer 212 will dry and bundle the biomass and weigh it prior to shipping. The cultivator/farmer 212 typically charges by weight. The weight will be used to create a manifest/bill of lading and combined lot number for the biomass which is memorialized in blockchain record 223 of the blockchain-based ledger 204 and can be referenced via a QR code printed on the manifest/bill of lading or a tamper-proof decal or sticker 206.

In one exemplary embodiment, physical indicia (or indicium) 206 can be attached to packaging for the tracked agricultural products and used to reference entries within the blockchain-based ledger 204. The exemplary physical indicia 206 is labeling that can quickly verify chain-of-custody in real-time using e.g., mobile connectivity and/or widely available broadband access. In one specific variant, the physical indicia may include a Quick Response (QR) Code printed on a tamper-proof decal or sticker (e.g., a decal or sticker that cannot be removed without destruction, commonly used within the law enforcement) to preserve chain-of-custody integrity.

In one exemplary embodiment, the physical indicia 206 may additionally include manifest/bill of lading information useful to validate the agricultural contents within the package with certainty. In one specific implementation, the manifest information may specify e.g., a weight, percentage by weight, a volume, percentage by volume, a density, genetic information, spectrographic sample, chemical composition, and/or other compliance information.

Within the context of the supply chain transport, the terms "validate" and "verify" are independent procedures that may be used together or in isolation to ensure that a product meets certain requirements and/or specifications. Specifically, validation refers to a measurement process that is calibrated and recorded for other parties to check objective conformance. For instance, a cultivator 212 may validate the contents of a manifest/bill of lading are hemp based on the aforementioned THC analysis (discussed in FIG. 2A, supra), and record validation information within the blockchain-based ledger 204. In contrast, verification refers to a process or metric that ensures that appropriate chain-of-custody protocols were followed. For instance, a law enforcement officer (LEO) 216 can verify that chain-of-custody was complied with by inspecting tamper-proof packaging and/or scanning physical indicia 206. Notably, validation and verification may entail different levels of complexity. Validation is always objective and may require expensive and accurate equipment (e.g., to weigh, measure chemistry, etc.); verification may be subjective and/or otherwise easily checked (e.g., visual inspection and a QR code scan.)

Each party within the supply chain may accept or deny custody of the package based on validation and/or verification of the manifest/bill of lading information; thus, in the event that the packaging is compromised, the chain-of-custody identifies the responsible party that is liable for custody of the package. Specifically, the agricultural package may be verified by ensuring that packaging is intact (e.g., that a tamper-proof sticker is intact, and that the packaging has not been torn or otherwise mutilated) and/or validated against the manifest/bill of lading information (e.g., that the measured weight, percentage by weight, volume, percentage by volume, density, genetic information, etc. matches the manifest/bill of lading information). In some cases, validation and/or verification protocols may be different for different participants; certain parties may e.g., only validate weight at commercial vehicle weight stations (not chemical composition, etc.)

A transporter 214 verifies and validates the manifest/bill of lading information before accepting custody of the package. Specifically, the transporter 214 visually inspects (verifies) the tamper-proof sticker 206, and validates that the manifest/bill of lading information (e.g., shipping weight) complies with the record 223; the record 223 can be retrieved based on the tamper-proof sticker 206. When the transporter 214 has successfully verified and validated the manifest/bill of lading information, the transporter 214 memorializes the change-in-custody via record 224.

In one exemplary embodiment, the cultivator 212 will load their biomass into a shipping container; once loaded, cultivator 212 can seal the shipping container with their cell phone using a smart lock. The exemplary smart lock is an Internet of Things (IOT) device that can be remotely controlled based on the blockchain state. The blockchain-based supply chain locks shipments between a source and a destination e.g., a source record locks the package until it is delivered to a destination on file (filed destination), the destination record opens the lock. In the illustrated scenario, once the manifest/bill of lading has been accepted for transport, the cultivator 212 locks the smart lock with blockchain record 225. Thereafter, neither the transporter 214 nor cultivator 212 alone can unlock the shipping container. The smart lock protects any intermediary during transit because they cannot be forced into opening the shipping container (much like an automatically locking cashier box). In some variants, the transporter 214 may also have a personal or smart lock mechanism to lock/unlock the shipping container during their custody.

During shipment, a law enforcement officer (LEO) 216 can verify that the shipping container has remained unopened, and that the current possessor matches the recorded chain-of-custody using a mobile application running on e.g., a smart phone or similar mobile device. Verification may be quickly performed by scanning the QR code and checking that the transporter 214 has complied with the chain-of-custody requirements. Additionally, the LEO 216 can review the manifest/bill of lading (with weights by the cultivator and vehicle weights obtained at highway weigh stations), and access prior DEA registered laboratory results. Law enforcement queries 226 (time, location, etc.) may be recorded within the blockchain-based ledger 204 to provide additional package tracking visibility.

In rare situations, the LEO 216 may need to interdict and/or breach the shipping container. If the LEO decides to open the sealed container, the LEO can assume custody of the load and request an override to open the smart lock. The blockchain mobile application may warn the LEO that opening the sealed cargo will trigger immediate notifications to the appropriate State and Federal authorities along with chain-of-custody updates to the blockchain ledger (transferring the package to the LEO). In the event that a LEO fails to use the blockchain mobile app, the driver, live tracking, and subsequent LEO paperwork can be manually uploaded into the blockchain to memorialize chain-of-custody termination. As before, immediate notifications will be made to the appropriate State and Federal authorities along with entries within the blockchain ledger regarding the transfer of custody.

After the package has reached its destination, both the transporter 214 and recipient (e.g., retailer 218) will be checked for proximity to the destination on file; proximity may be detected via geofencing, Bluetooth, or similar geospatial technology. When delivery conditions are satisfied (both parties are within a prescribed radius of the destination), the destination blockchain record 228 opens the smart lock. The transporter 214 can also remove their own sealing mechanism (if present).

In some cases, the retailer 218 may further process biomass for consumption/use e.g., hemp oil, CBD isolate, fiber, or any number or other products. The by-product can be sampled and tested for THC (similar to the process described in FIG. 2A, supra). By-products that do not contain more than 0.3% THC can be transported or sold to consumers without any further regulation within the United States (however international exportation may incur additional regulation).

The foregoing process ensures that the entire chain-of-custody, from "cradle-to-grave" is recorded. The granularity of data and transparency ensures that the entire lineage of agricultural product, and all associated logistics data, can be inspected by any interested party. More directly, the chain-of-custody is a critical element for traceability in the agricultural supply chain. Agricultural products are tested, weighed, sealed with a QR Code decal, smart locks and assigned custody throughout the supply chain management; all the data is memorialized within the agricultural blockchain-based ledger. Each link in the party is required to report deviation or alteration immediately (in real-time), to alert the regulatory agencies that a change and possible breach of seal or a break in the chain-of-custody has occurred.

In some cases, the chain-of-custody may be further bifurcated into different degrees of liability based on validation and/or verification requirements. For example, a "hot" truckload that has a different manifest/bill of lading weight may impose liability on the last party that weighed the hemp package (e.g., the transporter 214.) In contrast, a "hot" truckload that the same manifest/bill of lading weight may impose liability on the last party that validated the hemp's THC (e.g., the farmer/processor 212).

While the following examples are described in the context of hemp, the utility of the exemplary blockchain-based supply chain management described herein broadly applies to any agricultural product that might benefit from retrotracing and/or traceability. As previously alluded to, the existing agricultural supply chain cannot identify the source of goods. This is particularly problematic when e.g., an *E. coli* outbreak at a single farm results in the destruction of crops nationwide and subsequent market shortages because it is impossible to identify the source of the contaminant. Retro-traceability greatly facilitates contamination analysis.

Moreover, the exemplary blockchain-based supply chain management described herein may also decentralize supply chain management within existing agricultural industries. Historically, large scale industrialization of agricultural products drove small farmers to trade their independence for security. As a result, the vast majority of farmers in the U.S. are beholden to only a handful of food conglomerates. Some markets are willing to pay premium prices to support independent farming and/or boutique agricultural products (e.g., pasture raised beef, heritage pork, heirloom vegetables, cultivated oyster beds, etc.) A decentralized blockchain-based ledger enables any party (farmer, distributor, marketplace, etc.) to find, contact, and establish trade relationships in a trusted and transparent manner within the (vetted) network.

Furthermore, many agricultural products look very similar. Hemp is visually indistinguishable from marijuana; e.g., expensive chemical analysis is required to distinguish between the two. As another example, industrially farmed meat is visually quite similar to single sourced and heritage agricultural products despite significant differences in price. More directly, the exemplary chain-of-custody supply chain enables any party (law enforcement, customs official, customer, agriculture inspector, etc.) to verify the contents and/or agri-genomics of their produce with minimal training and/or everyday equipment (a mobile phone, etc.)

Still other applications for the exemplary blockchain-based supply chain described herein, may be readily substituted by artisans of ordinary skill in the related arts given the contents of the present disclosure.

Apparatus for Chain-of-Custody Based Enforcement

Figure 3:
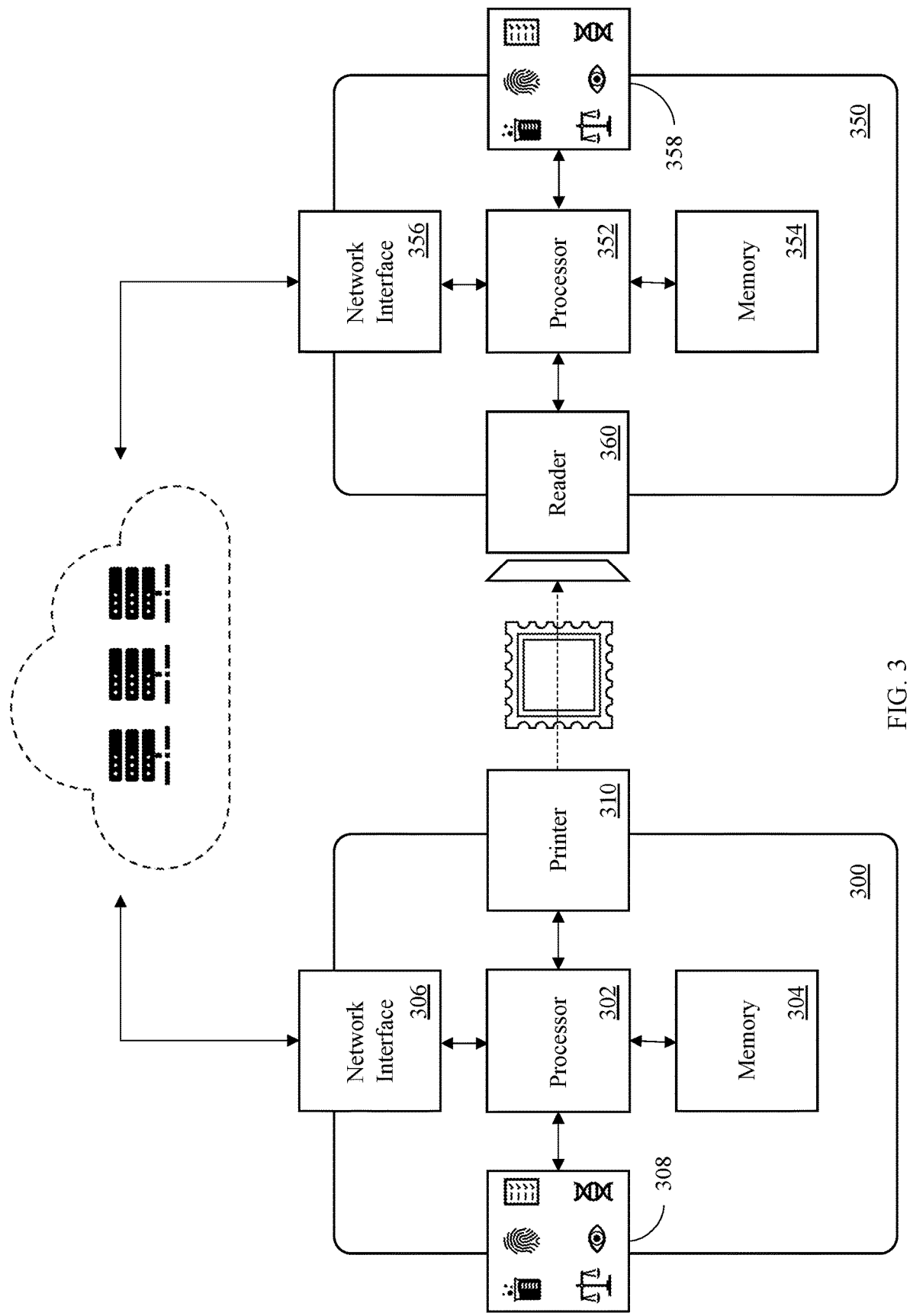
FIG. 3 is a logical block diagram of one exemplary system for chain-of-custody based enforcement, in accordance with the various principles described herein.

FIG. 3 is a logical block diagram of one exemplary system for chain-of-custody based enforcement. As shown therein, a labeling device 300 can generate physical indicia (or indicium) to mark physical assets. In one exemplary embodiment, the labeling device 300 may be a mobile device running a labeling application that enables a hemp cultivator to label their hemp biomass for transport. The physical indicia are a unique and unambiguous reference to a set of digital records associated with the physical assets. In one exemplary embodiment, the physical indicia may include a Quick Response (QR) Code printed on a tamper-proof self-adhesive sealing label. The inspecting device 350 can read physical indicia to inspect the physical assets. In one exemplary embodiment, the inspecting device 300 may be a mobile device running an inspection application used by different parties of the supply chain (e.g., transporter, law enforcement, and/or retailers) to validate and/or verify the chain-of-custody and/or integrity of the physical assets.

While the system of FIG. 3 depicts a labeling device 300 and an inspecting device 350, the principles described herein may be extended to any number of devices. More generally, a supply chain may (and likely does) incorporate many different parties e.g., creating, harvesting, manufacturing, distributing, selling, re-selling, delivering, inspecting, and/or otherwise tasked with handling goods. For example, a cultivator may harvest biomass, a transporter may transport biomass, law enforcement may inspect biomass, and retailers may re-sell biomass.

Additionally, the illustrated labeling device 300 and inspecting device 350 are depicted as singular devices, however the constituent functionality embodied therein may be distributed across any number of devices without limitation. For example, a cultivator may weigh biomass on a scale, input the weight into their mobile phone to obtain a QR code, and print the QR code on a printer (three separate devices). Similarly, the various functionalities may be combined into one or more devices; for example, a transporter may use the same mobile phone to both inspect and label packages. More directly, any consolidation, division, distribution, agglomeration, and/or combination of functionality may be substituted by artisans of ordinary skill in the related arts, given the contents of the present disclosure.

While the foregoing disclosure is presented in the context of human actors using devices, artisans of ordinary skill in the related arts will readily appreciate that the devices described herein are readily adapted to a variety of mechanized actors common in the supply chain and logistics arts. For example, machine readable physical indicia (such as QR codes) can be used for a variety of automation and/or robotic tasks. Similarly, hybrid human-machine readable physical indicia (such as bar codes and/or alphanumeric codes) may be used where human and/or machine actors may cooperate and/or interact.

In the illustrated embodiment, the labeling device 300 includes a processor apparatus 302, a non-transitory computer readable medium 304, a network interface 306, a sensor 308, and a printer 310. The inspecting device 350 includes a processor apparatus 352, a non-transitory computer readable medium 354, a network interface 356, a sensor 358, and a reader 360.

During operation, the processor apparatus (302, 352) reads software instructions from the non-transitory computer readable medium (304, 354) and executes the software to implement various functionalities. In one embodiment, the software instructions may be stored in the computer readable medium on a permanent or semi-permanent basis. Examples of such software may include firmware and/or "burned-in" software. In other embodiments, software instructions may be downloaded to the computer readable medium; examples of such software include e.g., mobile applications. In some cases, software downloads may require a registration and/or authentication authorization process; this may ensure that the device is downloading the software for legitimate use, etc.

While the present disclosure is presented in the context of a computer processor, other forms of processing logic may be substituted with equal success. Examples of processor logic include without limitation central processing units (CPUs), digital signal processors (DSPs), graphics processing units (GPUs), application specific integrated circuits (ASIC), system on a chip (SOC), programmable logic devices (PLDs), field programmable gate arrays (FPGAs), and/or any number of other computing devices. Memory logic may include random access memory and its variants thereof (RAM, SRAM, DRAM, SDRAM, etc.), read only memory and its variants thereof (ROM, EPROM, EEPROM, flash, etc.) Memory may be fixed or removable; examples of memory logic include without limitation: hard drives, flash storage, removable media, optical discs, and/or any other form of computer readable media.

In one embodiment, the labeling device 300 and inspecting device 350 communicate with a network via network interfaces (306, 356.) In one exemplary embodiment, the network interfaces may be wired or wireless internet connections. Examples of such network interfaces may include without limitation: cellular network connectivity, wireless local area network connectivity (e.g., IEEE 802.11 and its variants), personal area network connectivity (e.g., Bluetooth, RFID, etc.) More generally, any logic or apparatus that enables the devices to access or otherwise interact with a distributed ledger via a network may be substituted with equal success by artisans of ordinary skill in the related arts, given the contents of the present disclosure.

In one embodiment, the labeling device 300 and inspecting device 350 can physically sense one or more characteristics of the physical asset via sensors (308, 358). In one exemplary embodiment of the present disclosure, hemp biomass is weighed and/or tested for chemical composition. More generally however, any physical characteristic of the physical asset may be substituted with equal success by artisans of ordinary skill in the related arts, given the contents of the present disclosure. Examples of physical characteristics include without limitation: scent, weight, percentage by weight, volume, percentage by volume, density, size, dimension, coloration, structure, varietal, breed, genus, species, distinguishing marks (birth marks, etc.), genetic lineage, geographic information system (GIS) mapping of parcel, soils report, chemical/biological analysis, dry weight, and/or any other identifying information.

While the foregoing discussion is presented in the context of physical characteristics of the physical asset, other variants may track other information associated with the physical assets handling. In one exemplary embodiment, any financial transactions associated with the physical asset may also be recorded. Furthermore, certain assets may be subject to handling requirements (e.g., temperature, humidity, vibration, radiation, regulatory transport (import/export), etc.); in some cases, procedures and/or handling may be recorded in the form of a checklist (e.g., visual inspection, quality assurances, etc.) In other cases, assets may need a record of the handling and/or custody information. For example, a human handler may need to be identified by their e.g., fingerprints, eyeprints, voiceprints, driver's license (or other identification), hand signature, etc. Vehicles for transport may need to be identified by make/model, year, vehicle identification number, gross weight, color, license plate, etc.

In one embodiment, the labeling device 300 can print physical indicia (or indicium) on a substrate via a printer 310. In one exemplary embodiment, the physical indicia are tamper-proof self-adhesive sealing labels. While the foregoing discussion describes printed labels, virtually any manufacturable physical indicia may be substituted with equal success by artisans of ordinary skill in the related arts. Physical indicia may be manufactured from any material suitable for marking, imprinting, embedding, or otherwise rendering in a readable format. Examples of materials include paper, wood, plastic, metal, ceramic, and/or hybrids thereof (e.g., woven materials, impregnated materials, etc.) Fabrication techniques may include casting, labeling/painting/coating/plating, molding, forming, machining, joining, and/other any hybrid or variant thereof.

In one exemplary embodiment, the printer 310 prints Quick Response (QR) codes. More generally, the indicia may be human readable, machine readable, or a combination thereof. Examples of human readable indicia include alphanumeric codes, color codes, symbols, etc. Examples of machine readable indicia include e.g., RFID, QR codes, bar codes. In some cases, the physical indicia may include both human and machine readable components (e.g., a QR code with a human readable URL). In some cases, the physical indicia may be specifically designed to be readable by only a human or a machine; examples of human-only readable media include e.g., captcha based labeling, examples of machine-only readable media include e.g., RFID, ultraviolet (or extra spectral) inking, magnetic tape, etc.

In one embodiment, the inspecting device 350 is configured to read a substrate for physical indicia via reader 360. In one exemplary embodiment, the reader 360 is a camera that reads QR codes. More generally, virtually any reader technology may be substituted with equal success by artisans of ordinary skill in the related arts. Machine readers may detect visual, physical, and/or electro-magnetic indicia. Other examples of machine readers include e.g., barcode readers, RFID readers, pen readers, laser scanners, etc. In other variants, the inspecting device 300 may allow a human to read human readable physical indicia and provide the appropriate information via a user interface. For example, a human may read and input an alphanumeric code and/or affirmatively verify that packaging has not been ripped, damaged, tampered with, or otherwise compromised.

Methods for Chain-of-Custody Based Enforcement

As used herein, the term "chain-of-custody" refers to documentation that records the sequence of possession, intent, control, transfer, analysis, and/or disposition of a physical asset. In one embodiment, the chain-of-custody is a linked set of records. Linking may be based on chronological sequence, spatial path, title, and/or any hybrid or combination thereof. Each record ascribes custody and/or ownership to one or more entities. The chain-of-custody may be traced based on e.g., time, location, and/or any other ordering scheme.

As used herein, the terms "consignor" and "consignee" refer to endpoint entities of a shipment; for example, the consignor ships goods to the consignee. Typically, the endpoints of the shipment are the seller (consignor) and buyer (consignee) of the package, however other forms of consignment exist. For example, the consignor may transfer goods to a consignee for distribution; such schemes are commonly used in agricultural commodities. In such cases, delivery is the responsibility of the consignor, the consignee only receives a flat commission on the market sale of the goods (profit/loss are assumed by the consignor).

As used herein, the term "bailment" refers to an asset that is possessed by a "bailor" for a "bailee"; the bailee is responsible for the contents of the bailment whereas the bailor is responsible for handling the bailment. As used herein, the terms "breaking bulk", "break bulk", "broken bulk", "breaking the chain-of-custody", "break the chain-of-custody", and/or "broken chain-of-custody" refer to actions and/or conditions that convert responsibility for the contents of the bailment to the bailor. For example, a bailor may break bulk by opening a bailment; thereafter, the bailor is responsible for the contents of the bailment.

In view of the foregoing, a consignment may entail multiple bailments in the supply chain. For example, a hemp cultivator may consign hemp biomass to a hemp retailer (a consignment), via a number of intermediate shipping entities (bailments).

While the foregoing terms are borrowed from existing lexicography, they are distinct therefrom. Notably, the foregoing concepts are modified for use with the distributed ledger and practicalities of supply chain management across different regulatory regimes. As but one such example, a bailor may break bulk under a first regulatory regime, but not another. For example, Federal law may require different procedures from State law; thus, an entity may have broken bulk for the purposes of Federal law, but not State law, and vice versa. Similarly, a bailment may include multiple consignments. For example, multiple cultivators may use a common distributor to bundle their biomass; each cultivator may have a share of the proceeds for a bundle, however the distributor may be held responsible for the bundle's overall CBD/THC composition.

As used herein, the term "distributed ledger" refers to any database that is shared and synchronized across multiple independent entities based on a consensus mechanism. Blockchain chain databases are one form of distributed ledger, but any data structure distributed and consensually updated may be substituted with equal success by artisans of ordinary skill in the related arts.

Figure 4:
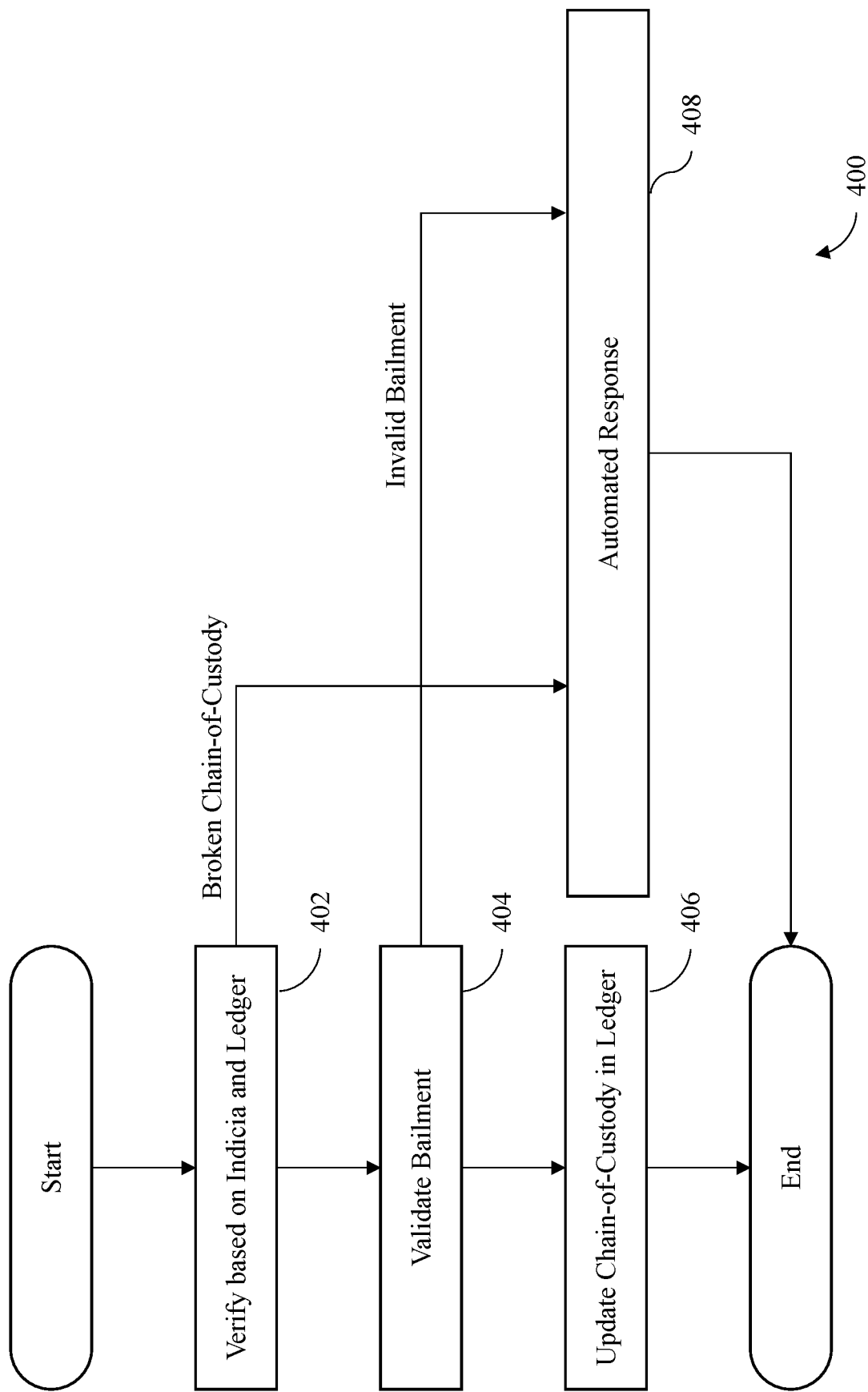
FIG. 4 is a logical flow diagram of an exemplary method for chain-of-custody based enforcement, in accordance with the various principles described herein.

Referring now to FIG. 4, one logical flow diagram of an exemplary method 400 for chain-of-custody based enforcement is shown. In one embodiment, a physical asset may be marked with one or more physical indicia; the one or more physical indicia associate the physical assets to digital records stored in a distributed ledger. Various information associated with the physical asset can be retrieved from the distributed ledger. In one exemplary embodiment, the distributed ledger stores a record of chain-of-custody and physical asset handling. The chain-of-custody record allows any independent regulatory entity to determine culpability at any time and/or location, based on their independent considerations. Thus, a chain-of-custody may enable e.g., multiple jurisdictions and/or commercial entities to operate independently, without coordination.

At step 402 of the method 400, an entity may verify a physical asset based on physical indicia (or indicium) and a distributed ledger. In one illustrative example, a law enforcement officer (LEO) may use a mobile application to scan a QR code on a shipment of hemp biomass; the QR code links to a blockchain ledger of transactions for the hemp biomass. The blockchain ledger identifies the current bailor and the current route, location/time, etc. In some cases, verification may also include inspection of the bailment. For example, a LEO can inspect packaging to determine whether or not a tamper-proof sticker is intact, and that the packaging has not been torn or otherwise mutilated.

In one embodiment, verification may include authentication and/or authorization of the bailor. Authentication refers to the process of identifying the bailor's identity, authorization refers to the process of determining the bailor's authorization to operate. For example, a LEO can determine whether a person in possession of the biomass matches the record (authenticated) and whether the person is permitted to operate in the location/time (authorized).

In one exemplary embodiment, verification may entail inspection (or the ability to inspect) the entire transactional history associated with a bailment. Based on the transaction history, the LEO can verify that chain-of-custody protocols and procedures have been followed (or broken) at any point in time. Similarly, a retailer can verify that proper chain-of-custody for hemp biomass has been followed before accepting custody (and accepting responsibility for the bailment). More generally, verification refers to the processes or metrics that ensure that the bailor (the entity in custody of the physical asset) matches the digital records of the distributed ledger. In the event that chain-of-custody is broken, then the bailor has broken bulk and is reported for automatic response (see step 408 of the method 400, described infra).

In one embodiment, the physical indicia provide a reference to data records stored within the distributed ledger. For example, reading a QR code identifies a set of digital records that are stored within a blockchain, corresponding to an agricultural product (e.g., hemp biomass, etc.). More generally, any technique for obtaining digital records associated with the physical assets may be substituted with equal success, given the contents of the present disclosure. In one alternative implementation, the physical indicia may be associated with the bailor or the bailee (rather than the bailment asset). For example, a transporter may carry an ID card with a magstripe (or similar readable indicia) that identifies the transporter and a history of the transporter's time and location. In another example, a cultivator may have an alphanumeric code (or similar readable indicia) to identify the cultivator's permitted activity. For example, a law enforcement officer may walk the cultivator's parcel of land to ensure that only tested crops are harvested into biomass. Other hybrids and variants may be substituted with equal success; for example, a transporter's magstripe ID card may be used in conjunction with a tamper evident QR code printed on the cargo.

In some cases, verification may entail a set of protocols and/or parameters that a bailor/bailee attests compliance to. As but one such illustrative example, a bailor may need to e.g., identify themselves, have appropriate licenses/permits, and provide a history of their whereabouts (locations/times). In some cases, the protocols and/or parameters may be publicly available and/or otherwise incorporated within the distributed ledger. For example, the bailor's identity, certification, and whereabouts may be recorded within records of the distributed ledger. In other cases, the protocols and/or parameters may be private, localized, or otherwise locally recorded at the entity. For example, the bailor may have locally stored digitally signed identity, certification, and locations/times. Still other variations may use a combination of the foregoing; e.g., verification may be based on both information stored locally and within the distributed ledger.

While the present disclosure is described in the context of human activity, machine entities may be substituted with equal success. As but one such example, drones may use wireless transponders and/or visual codes to monitor and verify human activity (e.g., surveying parcels of land, monitoring transporter fleets, etc.) Similarly, law enforcement officers may quickly scan QR codes to verify processing facilities, self-driving cars, etc. Any combination of human and/or machine verification may be substituted with equal success.

Additionally, while foregoing examples are illustrated in the context of physical possession, any exercise of intent and/or control may be substituted with equal success. For example, a transporter that has locked a physical asset with their own lock may have custody, even though they are not in direct physical proximity. Similarly, a transporter that has accepted (or failed to relinquish) custody of a physical asset in accordance with established protocols may be treated as having constructive or virtual custody (versus actual custody, or physical possession).

Referring back to FIG. 4, the entity may validate the bailment at step 404 of the method 400. Validation ensures that the bailment has remained intact (e.g., that the bailment is unchanged from its previously recorded state.) Validation may include both physical inspection as well as inspection of the historic record.

In one embodiment, the entity may retrieve historic records of the bailments previous state from the distributed ledger, based on the physical indicia. As but one such example, a transporter may use a mobile application to scan a QR code on a shipment of hemp biomass to retrieve a dry weight associated with the hemp biomass from the distributed ledger. The biomass is only valid if the currently measured dry weight is substantially similar to the previously recorded dry weight. In the event that the bailment fails validation, then a culpable bailee is identified and reported for automatic response (see step 408 of the method 400, described infra).

While the foregoing examples are presented in the context of dry weight and/or percentage by weight, virtually any physical characteristic may be used for validation. Common examples of physical characteristics used in agriculture include without limitation: scent, weight, percentage by weight, volume, percentage by volume, density, size, dimension, coloration, structure, varietal, breed, genus, species, distinguishing marks (birth marks, etc.), genetic lineage, geographic information system (GIS) mapping of parcel, soils report, chemical/biological analysis, dry weight, and/or any other identifying information.

Naturally occurring changes in the bailment may result in differences in measured characteristics; for example, dry weight may vary as a function of residual evaporation, off gassing, etc. Additionally, different regulatory bodies may establish different standards and/or calibration techniques that can result in differences in validation records. Consequently, in some embodiments, validation may be subject to a tolerance or include tolerancing information. Tolerances may be parameterized as absolute or relative percentages, maximum/minimums, etc. In some cases, measured variance within the tolerance may be considered acceptable. Alternatively, some jurisdictions may attribute failed validations to either the bailee or the bailor. For example, a transporter may need to plan their route, or a cultivator may need to limit their customer base, based on jurisdictional tolerancing.

At step 406 of the method 400, the entity may update the distributed ledger. Updating the distributed ledger may include adding a new record that attests to e.g., verification and/or validation information. Maintaining an up-to-date chain of records may allow for instantaneous review of the overall transaction. The chain of records may be used by many different parties for a variety of purposes. For instance, law enforcement can monitor the chain to determine where tampering may have occurred. Similarly, commercial entities may use the chain to monitor e.g., speed, cost, reliability, etc. In some cases, record updates may need to be performed after the fact; for example, poor network coverage may prevent timely updates. In such cases, timestamped updates may be queued for update; in some cases, the timestamped updates may be further digitally signed and/or cross-signed between peer devices so as to minimize the likelihood of falsification and/or to prevent malicious behavior. As described in greater detail herein, custody may be retained via bailor locks and ledger locks even when an entity is not in direct physical possession of a bailment.

Notably, the chain-of-custody provides a sequence of records that attest to the handling of the physical asset throughout the supply chain. As used herein, the term "attest", "attestation", and other variants thereof refer to an entity's declaration that they have verified and/or validated the physical asset (or bailment) at a specified location and/or time. A subsequent failed verification (e.g., a torn tamper evident sticker, etc.) can be traced between the last successful attestation and the point of failure.

In one embodiment, the entity may be required to authenticate and/or digitally sign the new record. In some variants, the entity may also be specifically authorized to attest to certain validations and/or verifications (e.g., an entity can only enter verification/validation information that the entity is qualified to attest to, etc.) In some embodiments, multiple entities may be required to authenticate and/or digitally sign the new record. For example, a weigh station may attest to dry weight subject to a transporter's approval; joint attestation may be useful to resolve subsequent disputes. In other embodiments, one entity may have an absolute authority to attest; for example, a DEA registered chemist/technician may have an unfettered ability to attest to THC percentage.

In some embodiments, an attestation may result in a change of custody. For example, the party making the most recent attestation may accept custody for the bailment; e.g., a transporter that attests to a dry weight is held responsible for the bailment's subsequent dry weight, previous dry weight attestations are superseded by the most recent attestation. In some cases, custodial relief may be partial; e.g., a bailor that has attested to multiple physical characteristics may only be relieved to the extent of the superceding attestation. For example, a shipper that only attests to dry weight may only be held responsible for subsequent dry weight validation; a cultivator that attests to a dry weight and a THC composition of a hemp biomass would be relieved of dry weight but may remain responsible for subsequent THC testing.

In some embodiments, different attestations may be held to different standards. As previously noted, different standards and/or measures may be calibrated to different levels of precision; entities with more precise measurement capabilities may be held to stricter compliance. Consider a first entity that attests accuracy to 1.0% tolerance and a second entity that attests accuracy to 0.5% tolerance; variation above 1.0% tolerance may impose responsibility on the first entity whereas variations between 0.5% and 1.0% may impose responsibility on the second entity.

Referring back to FIG. 4, in the event that chain-of-custody is broken, then the bailor has broken bulk. Conversely, if the chain-of-custody remains intact, but the bailment fails validation then a culpable bailee is identified. In either case, the validation and/or verification failures may be handled with an automated response.

In one exemplary embodiment, the automated response is based on regulatory requirements. Regulatory responses may vary depending on a variety of factors. Examples of such factors may include jurisdictional requirements, severity of infraction, a number of infractions, and/or a history of infractions. In one exemplary embodiment, hemp biomass that has a broken chain of custody and/or failed validation is impounded and law enforcement may be notified. In some cases, subsequent processing of the impounded bailment may also be handled using the distributed ledger; preserving the chain-of-custody for the impounded bailment may be necessary to comply with evidentiary requirements. In some cases, the bailment may be also be re-routed for state remediation processes.

In other embodiments, the automated response may be based on smart contracts and/or other negotiated stipulations. For example, contractual responses may be agreed upon ahead of time between the various parties (e.g., consignor, consignee, bailor, bailee, etc.) For example, a bailor that breaks bulk may be treated as a new bailee. In another case, a bailor that breaks bulk may owe damages to either the consignor (seller) and/or the consignee (buyer). Notably, fault can be identified to a specific party of the supply chain; failure to perform is transparent to every part from consignor to consignee.

More generally, chain-of-custody can be used to assign (or absolve) responsibility for any supply chain deviation activity. Failure to comply with chain-of-custody protocols can be flagged; thus, goods can be immediately flagged from transporters carrying untracked packages or monitored throughout a chain of commerce to identify multiple complicit parties. Participants can be absolved for activity they have no control over; culpability can be tracked back to the last responsible entity in the chain-of-custody. While the solutions described herein are motivated by incipient changes to the hemp industry, the techniques described herein are broadly applicable to any supply chain transaction. The distributed ledger enables parties to work together without assuming unknown risks; e.g., cultivators can work with transporters that they do not know, interstate banking institutions can lend money to unfamiliar businesses, etc.

Apparatus for Transferring Bailments

Figure 5:
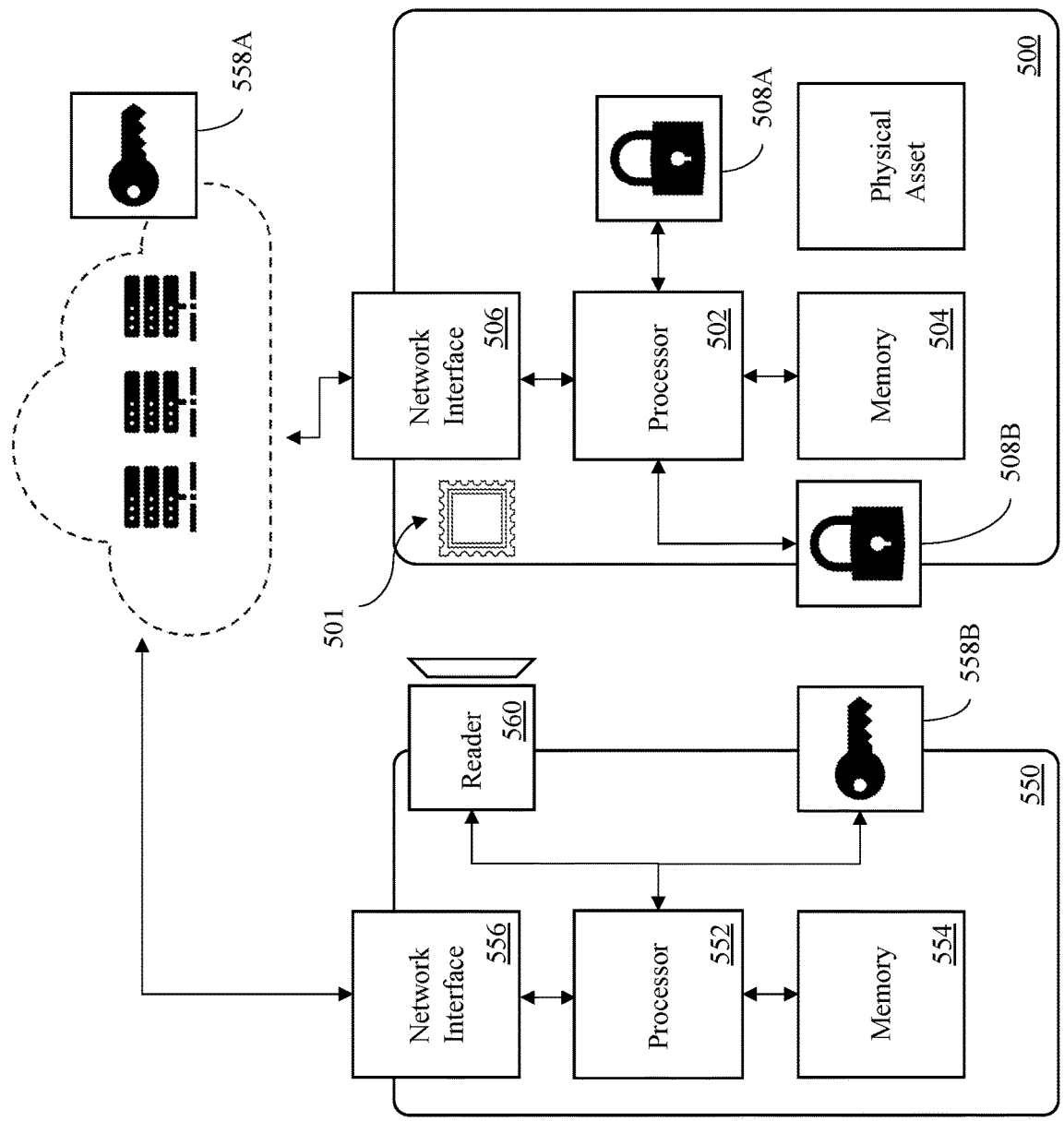
FIG. 5 is a logical block diagram of one exemplary system for transferring bailments, in accordance with the various principles described herein.

FIG. 5 is a logical block diagram of one exemplary system for transferring bailments. As shown therein, a physical asset is securely held within a smart bailment device 500. In one exemplary embodiment, the smart bailment device 500 may be a shipping container or similarly secure container (the physical assets may be further internally packaged within tamper-proof packaging). The smart bailment device 500 executes a distributed ledger lock application that secures the physical asset on route from a consignor to a consignee. While the illustrated smart bailment device 500 is typically locked for transit, there may be situations where a user may need to lock and/or unlock a user-specific lock while the physical asset is within their custody.

As shown in FIG. 5, the smart bailment device 500 may be marked with one or more physical indicia (or indicium) 501. The physical indicia are a unique and unambiguous reference to a set of digital records associated with smart locks 508A, 508B. In one exemplary embodiment, the physical indicia may include a Quick Response (QR) Code printed on the exterior of the smart bailment device 500. In one exemplary embodiment, a user device 550 can read the physical indicia to request or initiate a change in custody of the physical assets. In one exemplary embodiment, the user device 550 may be a mobile device running a mobile application used by different parties of the supply chain (e.g., consignor, consignee, bailor, bailee, etc.)

While the system of FIG. 5 depicts a smart bailment device 500 and a single user device 550, the principles described herein may be extended to any number of devices. As previously noted, a single bailment may be "in custody" by multiple entities. For instance, an entity that has locked a physical asset with their own lock may have custody, even though they are not in direct physical possession. Virtualized custody may enable multiple different parties to transparently work together; each party retains constructive custody of the physical asset (via their lock) until their release requirements are satisfied. More directly, any consolidation, division, distribution, agglomeration, and/or combination of functionality may be substituted by artisans of ordinary skill in the related arts, given the contents of the present disclosure.

While the foregoing disclosure is presented in the context of human actors using devices, artisans of ordinary skill in the related arts will readily appreciate that the devices described herein are readily adapted to a variety of mechanized actors common in the supply chain and logistics arts. For example, machine readable physical indicia (such as QR codes) can be used for a variety of automation and/or robotic tasks. Similarly, hybrid human-machine readable physical indicia (such as bar codes and/or alphanumeric codes) may be used where human and/or machine actors may cooperate and/or interact.

In the illustrated embodiment, the smart bailment device 500 includes physical indicia 501, a processor apparatus 502, a non-transitory computer readable medium 504, a network interface 506, one or more smart locks (508A, 508B). The user device 550 includes a processor apparatus 552, a non-transitory computer readable medium 554, a network interface 556, one or more smart keys (558A, 558B), and a reader 560.

During operation, the processor apparatus (502, 552) reads software instructions from the non-transitory computer readable medium (504, 554) and executes the software to implement various functionalities. In one embodiment, the smart bailment device 500 and user device 550 communicate with a network via network interfaces (506, 556.) In one exemplary embodiment, the network interfaces may be wired or wireless internet connections.

In one embodiment, the smart bailment device 500 includes one or more smart locks (508A, 508B). The smart locks are configured to lock the physical asset within the smart bailment device 500 until unlocked by smart key logic (558A, 558B). In some variants, all locks must be released before the physical asset may be accessed. In other variants, releasing any lock enables access to the physical asset. In still other variants, some locks may override other locks or vice versa. For example, the ledger key 558A may unlock any lock (508A, 508B), but each of the user locks 558B can only be unlocked by the user's specific key 508B. More generally, any combination of the foregoing may be substituted with equal success, the present disclosure being purely illustrative.

In one exemplary embodiment, the smart locks are configured to lock/unlock when provided with a mechanical key, electrical key, or hybrid thereof. Mechanical keys open and close a mechanism based on the structure of the key. Examples of mechanical locking mechanisms include without limitation: warded locks, tumbler locks (pin, wafer, disc, lever) and/or magnetic key locks. Electrical locks are usually implemented within secure software, firmware, or hardware; electrical locks open and close when provided with secret information (a key) usually via e.g., a code, password, token, challenge/response protocol, or similar cryptographic protocol. More generally, virtually any locking mechanism may be used to secure the smart bailment device 500.

In one exemplary embodiment, the smart locks include at least one ledger lock 508A. The ledger lock 508A is configured to lock or unlock when presented by a ledger key 558A that is generated and recorded within the distributed ledger. For example, an entity may request (or otherwise satisfy the conditions) to lock or unlock the ledger lock 508A. The distributed ledger generates a one-time key that is memorialized as a new record; the key is either delivered to the ledger lock 508A directly via its network interface 506 or provided to a user device for use when in spatial proximity and/or during a specified time window. In some variants, the ledger lock 508A may send an update when the key is actually used; this can prevent inadvertent lock-ups and/or other lock/unlock state mismatches.

In one exemplary embodiment, the smart locks include user locks 508B. The user locks 508B are configured to lock or unlock when presented by a user key 558B that is generated according to a user-specific system. For example, in some cases, a transporter may implement their own securitized system that is used for internal accountability. The user key 558B may be used with the user lock 508B; in such systems, user lock/unlock events may also be recorded within the distributed ledger.

Methods for Monitor and Control of a Supply Chain

As previously noted, supply chain and logistics management have historically been opaque to its constituents. Opacity naturally occurs as the supply chain network evolves in complexity, reliability, and redundancy. In ideal supply chains, each participant is a fungible node in the network. A supply chain participant that collapses, charges too much, is too slow, etc. is quickly replaced. More directly, each participant is insulated from other participants. Supply chains encourage participants to focus on optimizing their own costs and overhead for a small set of tasks. In other words, the overall supply chain reduces each participant's operating costs via massive economies of scale; participants maximize their revenue through specialization (the division of labor).

Regulatory requirements for hemp biomass are constrained by drug enforcement which imposes criminal jurisprudence standards for culpability (i.e., lack of knowledge is insufficient to escape liability). While the illustrative embodiments provide the requisite evidence of mens rea that enables hemp biomass supply chain operation, the various principles described herein are broadly applicable to any supply chain that benefits from decentralized monitoring and/or control over a consignment. Specifically, the various techniques described herein enable multiple parties to concurrently track and/or exercise custody over the bailment. More broadly, the distributed ledger described herein enables any number of organizations to cooperate in a fully decentralized manner, while preserving individual autonomy.

Figure 6:
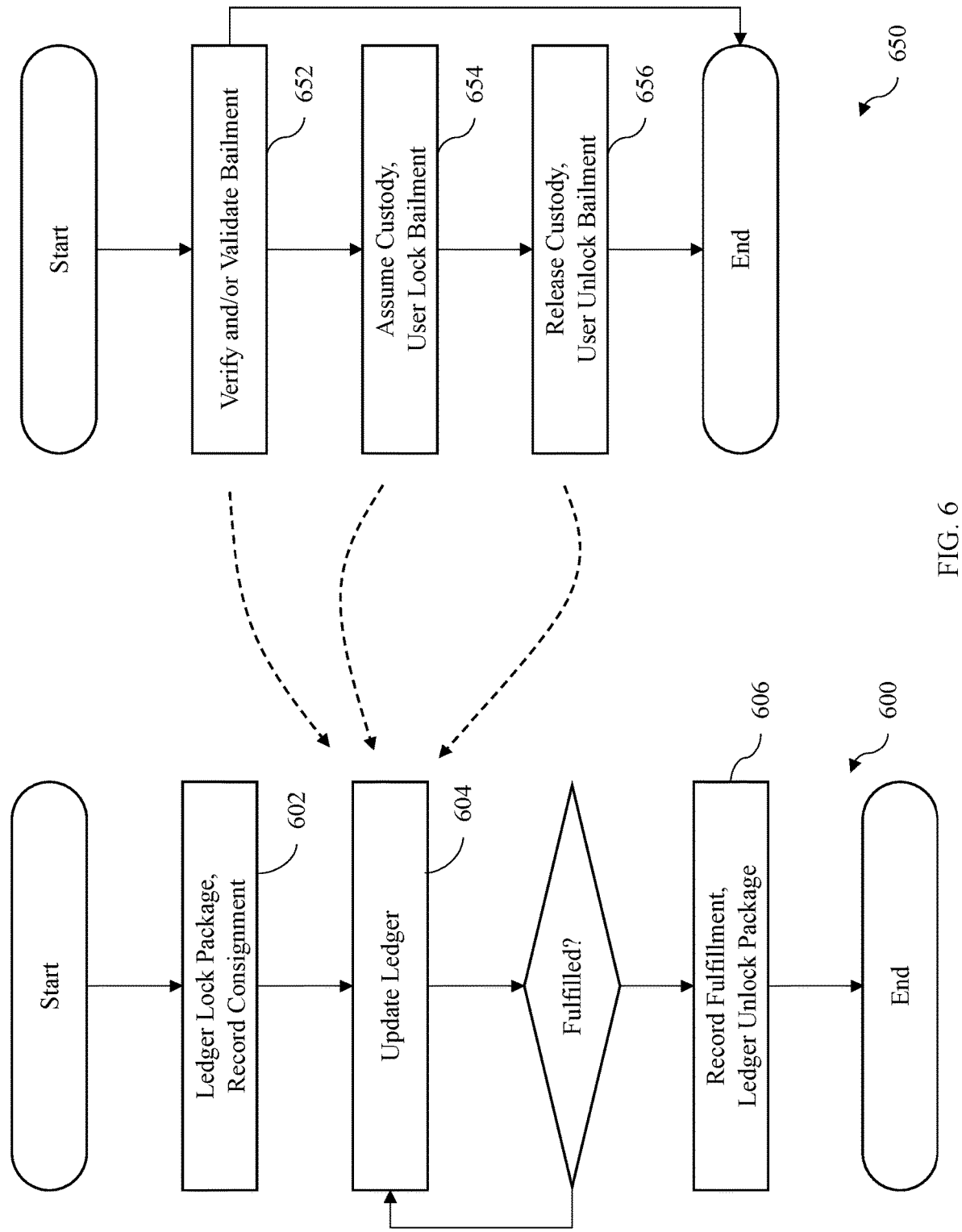
FIG. 6 is a logical flow diagram of an exemplary method for monitoring consignment via a distributed ledger, in accordance with the various principles described herein.

Referring first to method 600 of FIG. 6, one logical flow diagram of an exemplary method 600 for monitoring consignment via a distributed ledger is shown.

At step 602 of the method 600, a package is ledger locked for delivery, and a consignment is recorded within the distributed ledger. While the foregoing discussions are presented in the context of physical assets, artisans of ordinary skill in the related arts will readily appreciate that virtually any asset (e.g., physical, virtual, tangible, intangible, etc.) may be packaged for delivery. For example, computer readable medium containing virtual assets may be encrypted to prevent unauthorized use. In another such example, title to an intangible property (e.g., water and/or mineral rights) may be secured. More generally, the package may include any asset that can be secured from unauthorized use by another.

In one embodiment, the asset is secured within a physical vessel for delivery. In one exemplary embodiment, the physical vessel is mechanically locked via a ledger key generated by the distributed ledger. For example, hemp may be dried and packed into tamper-proof biomass parcels that are packaged within a smart locked shipping container. In another embodiment, digital assets may be digitally locked via a ledger key generated by the distributed ledger. For example, digital assets may be encrypted, encoded, scrambled, or otherwise obfuscated based on a ledger key.

In one embodiment, the consignment record identifies at least one endpoint for the package. In the illustrative examples described herein, consignment is associated with two endpoints, a consignor (the shipper) and the consignee (the recipient). More generally however, the consignment record may be "conditional." A conditional consignment record identifies the endpoint conditions for creating a consignment to enter (and exit) the supply chain. Conditional events for entry/exit may be based on e.g., entity identity, agent identity, functional entity, time, time window, location, location window, price, quantity, quality, validation-verification information, and/or any other termination condition.

As but one such example, a hemp cultivator may generate a partial consignment record for their crop that identifies the conditions under which their biomass may be sold (e.g., a minimum price per weight, a window of time, etc.) e.g., similar to a "put" option. Thereafter, the ledger locked package may sit in a warehouse (or similar storage) until suitable conditions for fulfillment exist. In such cases, (constructive) custody may revert to the original consignor or remain with one of the current bailees/bailors (even though they are not in physical possession). Similarly, a hemp processor may generate partial consignment records to buy biomass under specified conditions (e.g., a maximum price per weight, a window of time, etc.) e.g., similar to a "call" option. In such conditions, the ledger locked package may be fulfilled by any cultivator that can answer the call option.

While the present disclosure is presented in the context of an end-to-end consignment, other transactions may be substituted with equal success by artisans of ordinary skill in the related arts. For example, some supply chains may redistribute goods based on e.g., history, popularity, etc. As but one such example, biomass may be preemptively moved to certain "hot" markets in anticipation of future demand. Still other techniques for hedging for/against market demand may be substitute with equal success by artisans of ordinary skill in the related arts, given the contents of the present disclosure.

At step 604 of the method 600, the distributed ledger may be updated with records throughout the supply chain until the consignment is fulfilled. Examples of records may include e.g., status updates (e.g., location, time), verification and/or validation updates, custody updates (assumption, release, suspension, override, etc.), regulatory events (e.g., taxation, inspection, impound, etc.), and/or any other supply chain events.

In one exemplary embodiment, records may be selectively added. For example, the distributed ledger may impose a consensus mechanism to ensure that the distributed ledger reflects the consensual state of the network. In some cases, the consensus mechanism may be a voting mechanism. Examples of consensus mechanisms include e.g., proof-of-work, proof-of-stake, proof-of-space, proof-of-connectivity. More generally, any consensus mechanism that transforms a limited quantity or token (processing power, memory, ownership, bandwidth, etc.) into a digital quantity or token (e.g., votes) ensures that the "infinite reproducibility" problem inherent to digital data is not abused.

While the present disclosure is presented in the context of a blockchain ledger that only adds new records, other distributed ledger data structures may be substituted with equal success by artisans of ordinary skill in the related arts. For example, other forms of distributed ledger may enable record addition, removal, modification, duplication, and/or rearrangement.

Additionally, while the present disclosure is discussed in the context of distributed ledgers, various aspects of the present disclosure may be applicable to centralized organizations and/or quasi-centralized organizations. For example, many businesses have naturally aggregated into loosely coupled, self-organizing networks, also called "extended enterprises". Extended enterprises may organize, and structure operation based on e.g., long term contractual agreements and/or joint corporate structuring. Examples of extended enterprises include horizontally and/or vertically integrated businesses (e.g., a corporation and sole suppliers, a franchiser and its franchisees, etc.) While not strictly centralized nor distributed, extended enterprises often have important aspects of both. For instance, horizontal peers in an extended enterprise may be competitive with one another and/or unlikely to cede independence to a centralized authority. Similarly, vertically organized participants may need the ability to transparently monitor critical nodes of the supply chain.

Referring back to FIG. 6, when the consignment is fulfilled the distributed ledger can unlock the package at step 606 of the method 600. In one exemplary embodiment, the consignment is fulfilled when it is successfully delivered to the consignee. In other embodiments, the consignment is fulfilled when the endpoint conditions for exiting the supply chain are satisfied.

More generally, the exemplary smart contract protocol and distributed ledger described herein may be used to transparently and securely link parties who have never done business before. This may be particularly useful for niche markets; e.g., an artisanal farmer can advertise and/or store their wares until they find a suitable buyer. Similarly, niche markets can generate requests for unusual commodities that are filled. The ledger locked consignment scheme ensures that the assets are delivered as originally packaged (an unauthorized intermediate entity cannot break bulk.)

While the various techniques described herein ideally enable an unbroken delivery, there may be situations where a consignment record is broken or otherwise left unexecuted/inexecutable. For example, regulatory entities may have the ability to override a ledger lock. Similarly, a put or call that is left unfulfilled may abort the consignment; nonetheless, since the ledger maintains an immutable record of ownership and/or custody, the assets remain ledger locked and may be re-assigned to a new consignment.

Referring first to method 650, one logical flow diagram for assuming and releasing custody of a bailment is shown. As previously noted, a consignment may entail multiple bailments; in fact, in some cases, a bailment may have multiple concurrent bailors in various states of actual and/or constructive custody. For example, a first entity may have physical possession (actual custody) of the bailment, while another entity may have constructive custody of the bailment.

At step 652 of the method 650, a prospective bailor may verify and/or validate a bailment prior to assuming custody. As described elsewhere herein, validation and verification are independent procedures that may be used together or in isolation to ensure that a product meets certain requirements and/or specifications. Assumption of custody imputes culpability to the bailor to the extent that the bailor has attested, thus every bailor is incentivized to attest to their validation and/or verification procedures truthfully. As a related benefit, a prospective bailor will report bailments immediately to avoid unnecessary liability exposure; as a result, the principles described herein incentivize every node of the supply chain to report issues immediately.

In one exemplary embodiment, the prospective bailor's validation and/or verification may be set based on regulatory requirements. For example, a transporter may need to verify packaging and/or validate dry weight as a matter of process; failure to perform validation and/or verification may impose regulatory enforcement. In other embodiments, the prospective bailor's validation and/or verification may be individually set. Certain entities may offer validation and/or verification as a value-added service; in some cases, the transparency of supply chain operation may be priced at a premium. For example, artisanal grocers may be incentivized to source agricultural produce from parties that validate/verify lineage via genetic testing, etc.

In one exemplary embodiment, validation and/or verification results may be memorialized within records of the distributed ledger. In some cases, validation and/or verification results may also be documented with the bailment (e.g., via bill of lading and/or manifest paperwork). In some variants, a bailor's failure to validate or verify a record may be a constructive validation or verification; constructive validation/verification may be imposed where regulatory restrictions require bailor compliance. In other variants, a bailor may accept custody without validation/verification; in certain cases, the bailor's procedures may be noted in the distributed ledger (e.g., a reduced service bailor may not be able to charge the same premiums for handling).

Once the bailor has accepted custody, the bailor may lock the package with a bailor specific lock (step 654 of the method 650) and/or release custody and unlock the package (step 656 of the method 650). In one exemplary embodiment, bailor custody status and/or smart lock control may be recorded and/or controlled via the distributed ledger.

In one exemplary embodiment, bailor custody updates identify the current party in custody of the bailment. As previously noted, custody refers to a bailor's intent/control over the bailment. Any number of bailors may have actual and/or constructive custody; for example, a cultivator and a driver may both seal a shipping container with their respective smart locks. Since both cultivator and the driver have independent control over the shipping container (the ability to exclude unauthorized use), both parties have custody: the cultivator has constructive (virtual) custody, and the driver has actual (physical) custody.

In one exemplary embodiment, bailor custody records may include: bailor/bailee identification, consignor/consignee identification, entity registration information, bill of lading/manifest information, validation/verification information (e.g., weight, percentage by weight, volume, percentage by volume, density, size, dimension, coloration, structure, varietal, breed, genus, species, distinguishing marks (birth marks, etc.), genetic lineage, geographic information system (GIS) mapping of parcel, soils report, chemical/biological analysis, dry weight, and/or any other identifying information.)

As a brief aside, due to the sophisticated nature of the drug trade, forensic accounting is often used to identify financial activity that can be indicative of money laundering, suspicious transactions, and/or other illicit financing activity. As previously noted, the Financial Crimes Enforcement Network (FinCEN) monitors banking activity and can freeze financial institutions for any infraction. Various embodiments of the present disclosure track proceeds throughout the lifecycle of the commodity (e.g., hemp biomass). Every financial transaction is recorded within the distributed ledger to maintain traceability. In this manner, forensic accounting can track proceeds from origin to destination; traceability can identify commingling of illicit and licit funds (money laundering).

In some such embodiments, custody records may include records regarding financial transactions; examples of financial transactions may include without limitation: transfer, escrow, disbursements, reimbursements, debts, credits, refunds, taxes, duties, and/or any other currency manipulation. In one exemplary embodiment, all currency movement within the supply chain is limited to financial institutions that are certified for use by regulatory bodies. For example, in the context of the hemp industry, financial transactions may be limited to financial institutions that are registered with the Financial Crimes Enforcement Network (FinCEN). More generally, however, other supply chain applications may be more or less lenient. Some such variants of the distributed ledger may only recognize a common cryptocurrency. In other variants, the distributed ledger may recognize any financial institution. In still other variants, financial recording may be informative or otherwise entirely extraneous (e.g., accounting, enforcement, guarantee, and/or surety may be external to the supply chain).

While the present disclosure is illustrated in the context of consignments (between endpoints) that are tracked within a distributed ledger, artisans of ordinary skill in the related arts will readily appreciate that bailor locked bailments may extend protection beyond the tracked consignment. In other words, even though the ledger lock ensures that a package is not tampered with through the supply chain, the bailor may be assured that the bailor-locked package can also be pristinely trafficked outside of the supply chain.

Additionally, the illustrated embodiments are described in the context of a bailor that is physically co-located to the package, however co-location is not required. In some cases, a bailor may remotely lock/unlock the bailment when their custody conditions are met. For instance, the bailor may remotely assume virtual custody when e.g., the bailment is validated or verified by a bailor's agent or other trusted party. The bailor may be notified that the bailment has arrived at its destination, and the bailor may remotely remove their lock. In other words, the bailor's custody may be entirely virtual; locking/unlocking may be performed remotely from the bailment. In another example, a bailment that has failed validation can be immediately bailor locked (i.e., remotely impounded), thereafter law enforcement officers (LEOs) can be dispatched to interdict/breach the locked container in situ.

Unlike systems that treat links in the supply chain as a "black box", various embodiments of the present disclosure enable multiple parties to concurrently monitor and control a common bailment. Bailments may be packaged together, split apart, merged, routed, re-routed, stored, or re-packed into different consignments, and vice versa. Throughout a bailment's route, different bailors may have different reasons for monitoring status, as well as asserting (or deferring) control of the bailment. Thus, while one participant may have actual custody at any point in time, any (all) of the virtual custodians can prevent unauthorized activity. In other words, the distinctions between consignments (a chain-of-custody) and bailments (an individual link of custody) enables a far more flexible scheme, that empowers any party according to their own considerations, responsibilities, and/or incentives.

As a brief aside, large financial institutions service a myriad of different industrial sectors, with different characteristics; additionally, client privacy considerations often limit regulatory oversight. Currently, commingled proceeds and illicit funds can only be discerned by manual forensic accounting and investigatory practices. Thus, forensic accounting is primarily used after other illicit activity is found; e.g., an alleged drug trafficker's accounts can be manually inspected by forensic experts for illicit activity, however automated identification of illicit activity in a sea of financial transactions is impractical for a variety of technical and legal reasons. To these ends, various embodiments of the present disclosure provide transparency into both assets and their corresponding proceeds.

In one exemplary embodiment, system-wide currency transaction traceability enables regulatory oversight over all transactions for a commodity-specific supply chain. Financial oversight of the industrial hemp market can be used to identify suspicious transactions and/or volumes of trade. Different industries have different revenue characteristics; e.g., certain industries carry large amounts of liquidity, whereas other industries may be credit driven, etc. Undifferentiated financial monitoring is impractical to identify anomalous behavior. In contrast, a commodity-specific supply chain is characterized by many different players transacting a fungible commodity (and services associated therewith). Pricing for substantially interchangeable commodities and services trend toward equilibrium; thus, non-competitive high or low volumes, unusual pricing, etc. can be readily identified.

In related embodiments, historic transactions can be used to flag anomalous behavior. Since an entity's entire history of financial transactions are transparently memorialized in the distributed ledger; anomalous behavior can be detected with e.g., running averages, pattern matching, machine learning, and/or any other anomaly detection scheme. As a brief aside, three broad categories of anomaly detection techniques exist. Unsupervised anomaly detection techniques detect anomalies in an unlabeled test data set under the assumption that the majority of the instances in the data set are normal; anomalies are instances that are statistical outliers of the data set. Supervised anomaly detection techniques require a data set that has been labeled as "normal" and "abnormal" (e.g., known forensic accounting data sets). Semi-supervised anomaly detection techniques construct a model representing normal behavior from a given normal training data set, and then test the likelihood of a test instance to be generated by the learnt model.

Notably, anomaly detection may be greatly improved by minimizing unrelated data, maximizing the quality of the training data, and/or increasing training set quantity. The exemplary embodiments described herein completely and transparently memorialize every consignment from consignor to consignee, every data record may be classified based on the record contents, and existing financial institutions are incentivized to cooperate by reporting anomalous behavior when detected. In other words, anomaly detection techniques substantially improve as the distributed ledger increases in size and usage.

Additionally, the preservation and transparency of every financial transaction can be used to automate forensic accounting. The transparent nature of the distributed ledger enables a thorough review of transactional history whenever/wherever required. Forensic accounting can be performed on a rolling basis to provide up-to-date analysis and/or batched for processing efficiency. In other words, the immutability of the distributed ledger removes time urgency. Furthermore, the vetted blockchain network creates a closed financial ecosystem. There are no blind spots, thus anomalies may be readily identifiable with ingress/egress monitoring (or other forensic accounting techniques). Market prices and financial transactions can be estimated according to historic equilibriums; unlike differentiated markets, single commodity markets trend to stable prices. For example, AML can predict the approximate gross product at any point in the supply chain. Any illicit currency infusion would lie outside the predictive parameters and may be flagged as suspicious. Flagged transactions also affect the reliability of all downstream transactions associated with the anomaly, thus incentivizing immediate scrutiny and cooperative action by the network members.

While the foregoing discussion is presented in the context of financial regulation and oversight, the principles described herein may be broadly applicable to a variety of supply chain participants. Various embodiments of the present disclosure may provide entities with different levels of access to a limited subset of capabilities based on privilege and/or access restrictions. For example, participants in the agricultural supply chain may be able to view and discover supply chain activity; e.g., a farmer may be able to see the status of their shipments, local markets that fetch the best prices, transporters that work the fastest, least expensive, etc. Local markets can directly source hemp and/or CBD from independent farmers, etc.

APPENDIX A provides a tabular listing of a myriad of illustrative smart contracts useful in accordance with the principles described herein. As shown therein, the "user groups" (e.g., "administrator", "clone botanist or seed distributor", "chemical laboratory", etc.) identify different participants that have access to the blockchain-based supply chain. The "smart contract blocks" identify types of smart contracts that may be formed between different participants. As but one such example, the user "USDA, Hemp Program" can issue a variety of different permits to other participants; the issued permits are stored within the blockchain-based ledger. As but another example, "non-government users" can generate and read Quick Response (QR) codes (described in greater detail, infra); QR code generations/reads are tracked within the blockchain-based ledger. Certain actions are not permitted; for example, a "clone botanist or seed distributor" cannot test for THC, etc. Notably, APPENDIX A is purely illustrative, and may be modified, extended, and/or redacted by artisans of ordinary skill, given the contents of the present disclosure.

While APPENDIX A provides an illustrative set of read/write privilege and/or access restrictions within the blockchain-based ledger, other access controls may be substituted with equal success. Common access controls may include, without limitation, read-only, read-write, write-only, lock/unlock (prevent write access), hide/unhide (prevent read access), search, filter, and/or variations thereof.

APPENDIX B provides an exemplary sequence of events for hemp agriculture, a set of requirements for implementing an agricultural blockchain-based ledger data structure and corresponding business methods for use.

Various user groups can access the agricultural blockchain-based ledger via a portal website, desktop application, and/or mobile applications executed from client-side devices. APPENDIX C provides an exemplary user interface and logic flow consistent with one exemplary implementation of the present disclosure.

Still other applications for the exemplary blockchain-based supply chain described herein, may be readily substituted by artisans of ordinary skill in the related arts given the contents of the present disclosure. APPENDIX D provides further discussion relating to current events and/or benefits of the present disclosure.

It will be appreciated that the various ones of the foregoing aspects of the present disclosure, or any parts or functions thereof, may be implemented using hardware, software, firmware, tangible, and non-transitory computer-readable or computer usable storage media having instructions stored thereon, or a combination thereof, and may be implemented in one or more computer systems.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A method for real-time chain-of-custody based enforcement, comprising:
reading physical indicia of a bailment to retrieve a set of records from a distributed ledger associated with the bailment;
verifying a custody record of the set of records for the bailment where the custody record identifies an authorized area and a current route of the bailment;
measuring a physical characteristic of the bailment;
validating that the physical characteristic matches a previously recorded measurement record of the set of records for the bailment;
determining a current location of the bailment via a geospatial system; and
adding a new an attestation record to the distributed ledger to record a partial custodial relief in real-time at the current location.

2. The method of claim 1, wherein reading the physical indicia of the bailment comprises scanning a quick response code printed on a physically intact tamper-proof label; and
wherein the set of records are retrieved from a blockchain-based ledger based on the quick response code.

3. The method of claim 1, wherein verifying the custody record comprises determining that an identity of a person in possession of the bailment matches the custody record.

4. The method of claim 1, wherein verifying the custody record comprises determining that a current location of the bailment matches the custody record.

5. The method of claim 1, wherein verifying the custody record comprises determining that a previous location of the bailment matches the custody record.

6. The method of claim 1, wherein measuring the physical characteristic of the bailment comprises measuring a dry weight; and
the previously recorded measurement record comprises a previously measured dry weight.

7. The method of claim 1, wherein measuring the physical characteristic of the bailment comprises measuring a chemical composition; and
the previously recorded measurement record comprises a previously chemical composition.

8. An apparatus for real-time chain-of-custody based enforcement, comprising:
a reader configured to read physical indicia;
a geospatial subsystem configured to determine a current location of a bailment;
a network interface configured to communicate with a distributed ledger;
a processor; and
a non-transitory computer-readable medium comprising one or more instructions which when executed by the processor, cause the apparatus to:
read the physical indicia of the bailment;
retrieve a set of records associated with the physical indicia from the distributed ledger associated with the bailment, where the set of records comprises a custody record that identifies an authorized area and current route; and
report the bailment for regulatory response when the set of records does not match the bailment.

9. The apparatus of claim 8, further comprising logic configured to identify a person in possession of the bailment; and
where the set of records includes a first custody record that identifies an authorized bailee.

10. The apparatus of claim 8, further comprising logic configured to identify a source or destination of the bailment; and where the set of records includes a consignment record that identifies at least one of a consignor and a consignee.

11. The apparatus of claim 8, further comprising a sensor configured to measure a physical characteristic of the bailment; and where the set of records includes a previously measured physical characteristic of the bailment.

12. The apparatus of claim 11, wherein the sensor measures a dry weight of the bailment.

13. The apparatus of claim 11, wherein the sensor measures a chemical composition of the bailment.

14. An apparatus for real-time chain-of-custody based enforcement, comprising:
   a reader configured to read physical indicia;
   a network interface configured to communicate with a distributed ledger;
   a processor; and
   a non-transitory computer-readable medium comprising instructions which when executed by the processor, cause the apparatus to:
      read the physical indicia of a bailment;
      retrieve a set of records associated with the physical indicia from the distributed ledger associated with the bailment, where the set of records identifies a plurality of previous locations of the bailment; and
      report the bailment for regulatory response in a current jurisdiction based on at least one previous location of the bailment.

15. The apparatus of claim 14, where the apparatus comprises a geospatial subsystem configured to determine a current location of a bailment.

16. The apparatus of claim 14, where the reader comprises a camera configured to read quick response codes, the network interface comprises a cellular network interface, and the apparatus is associated with a law enforcement officer.

17. The apparatus of claim 16, where the instructions, when executed by the processor, further cause the apparatus to record a time, a location, and a query of the bailment made by the law enforcement officer.

18. The apparatus of claim 17, where the instructions, when executed by the processor, further cause the apparatus to:
   transmit a request to override a smart lock associated with the bailment; and transfer custody of the bailment to the law enforcement officer.

19. The apparatus of claim 14, where the set of records comprises a custody record that identifies an authorized area and current route.

* * * * *